(12) United States Patent
Diehl et al.

(10) Patent No.: US 9,005,478 B2
(45) Date of Patent: Apr. 14, 2015

(54) 2,2'-BINAPHTHALENE ESTER CHIRAL DOPANTS FOR CHOLESTERIC LIQUID CRYSTAL DISPLAYS

(71) Applicants: Donald R. Diehl, Rochester, NY (US); Erica N. Montbach, Kent, OH (US)

(72) Inventors: Donald R. Diehl, Rochester, NY (US); Erica N. Montbach, Kent, OH (US)

(73) Assignees: Kent Displays Incorporated, Kent, OH (US); Kent State University, Kent, OH (US)

( * ) Notice: Subject to any disclaimer, the term of this patent is extended or adjusted under 35 U.S.C. 154(b) by 0 days.

(21) Appl. No.: 14/147,730

(22) Filed: Jan. 6, 2014

(65) Prior Publication Data

US 2014/0117284 A1 May 1, 2014

Related U.S. Application Data

(62) Division of application No. 13/593,971, filed on Aug. 24, 2012, now Pat. No. 8,709,281.

(51) Int. Cl.

| | |
|---|---|
| C09K 19/32 | (2006.01) |
| C09K 19/58 | (2006.01) |
| C07C 69/76 | (2006.01) |
| C07C 49/00 | (2006.01) |
| C07C 255/57 | (2006.01) |
| C07D 321/00 | (2006.01) |
| C07D 321/10 | (2006.01) |
| C07D 321/12 | (2006.01) |

(52) U.S. Cl.
CPC .......... *C09K 19/586* (2013.01); *C07C 255/57* (2013.01); *C07D 321/00* (2013.01); *C07D 321/10* (2013.01); *C07D 321/12* (2013.01); Y10T 428/10 (2015.01); C09K 2019/323 (2013.01)

(58) Field of Classification Search
CPC .......... C09K 19/586; C09K 2019/323; C07C 255/57; C07D 321/00; C07D 321/10; C07D 321/12; Y10T 428/10
USPC ............ 252/299.2, 299.62; 428/1.1; 349/182; 560/56, 80, 100; 568/328
See application file for complete search history.

(56) References Cited

U.S. PATENT DOCUMENTS

| | | | |
|---|---|---|---|
| 3,761,526 | A | 9/1973 | Houlihan et al. |
| 4,826,620 | A | 5/1989 | Heppke et al. |
| 5,089,530 | A | 2/1992 | Tsipouras et al. |
| 6,699,532 | B2 | 3/2004 | Motoyama et al. |
| 7,413,782 | B2 | 8/2008 | Kato et al. |
| 8,709,281 | B2 * | 4/2014 | Diehl et al. ............... 252/299.62 |

FOREIGN PATENT DOCUMENTS

| | | |
|---|---|---|
| CN | 1900694 | 1/2007 |
| JP | 2009209118 | 9/2009 |
| JP | 2010047524 | 3/2010 |
| JP | 2011256119 | 12/2011 |
| WO | 0056691 | 9/2000 |
| WO | 0234739 | 5/2002 |

OTHER PUBLICATIONS

M. Bauer, et al., Evaluation of chiral dopants for LCD applications, Journal of the SID (2006), 14/9, 805-812.
G. Chai, et al., Studies on the Tandem Reaction of 4-Aryl-2,3-allenoates with Organozinc Reagents: A Facile Route to Polysubstituted Naphthols, Chemistry—A European Journal (2009), 15, 11083-11086.

(Continued)

*Primary Examiner* — Geraldina Visconti
(74) *Attorney, Agent, or Firm* — Pearne & Gordon LLP

(57) ABSTRACT

A liquid crystal composition comprising a chiral dopant compound represented by the following structure (Structure 1):

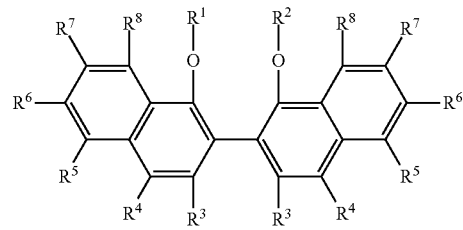

wherein:
R1 and R2 are independently hydrogen, —(C=O)R9, —(C=O)R10, alkyl, aryl, alkaryl, alkenyl, cycloalkyl, alkoxyaryl, or heterocyclic all either substituted or unsubstituted, or combine to form a carbocyclic or heterocyclic ring;
R3 is hydrogen, halogen, cyano, alkoxy, NHCOR9, NHSO2R9, COOR9, OCOR9, aryl, alkyl, alkenyl, cycloalkyl, or heterocyclic all either substituted or unsubstituted;
R4 is hydrogen, alkyl, aryl, alkenyl, cycloalkyl, or heterocyclic all either substituted or unsubstituted;
R5, R6, R7, and R8 are independently hydrogen, halogen, cyano, alkoxy, NHCOR9, NHSO2R9, COOR9, OCOR9, aryl, alkyl, alkenyl, cycloalkyl, alkoxyaryl or heterocyclic all either substituted or unsubstituted, or combine with each other, or R5 can combine with R4 to form a carbocyclic or heterocyclic ring;
R9 and R10 are independently alkyl, alkoxy, aryl, naphthyl, styryl, alkenyl, cycloalkyl, alkoxyaryl, cycloalkoxy, or heterocyclic all either substituted or unsubstituted, or combine to form a carbocyclic or heterocyclic ring. Also featured are liquid crystal compositions comprising a chiral dopant compound represented by any of Structure 2-4.

21 Claims, No Drawings

(56) References Cited

OTHER PUBLICATIONS

Z. Ding et al., Scalable Syntheses of the Vaulted Biaryl Ligands VAPOL and VANOL via the Cycloaddition/Electrocyclization Cascade, Organic Process Research & Development (2011), 15, 1089-1107.

R. Eelkema and B. Feringa, Amplification of chirality in liquid crystals, Organic & Biomolecular Chemistry (2006), 4, 3729-3745.

G. Gottarelli and G. Spada, Induced Cholesteric Mesophases: Origin and Application, Molecular Crystals and Liquid Crystals (1985), 123, 377-388.

G. Gottarelli, et al., Induction of the Cholesteric Mesophase in Nematic Liquid Crystals: Mechanism and Application to the Determination of Bridged Biaryl Configurations, Journal of the American Chemical Society (1983), 105, 7318-7321.

T. Hamura, et al., Tandem Ring Expansion of Alkenyl Benzocyclobutenal Derivatives into Substituted Naphthols, Angewandte Chemie International Edition (2006), 45, 6294-6296.

P. Henderson, et al., Antiferroelectric Liquid Crystals Containing a Naphthoate Mesogenic Unit, Ferroelectrics (2006), 343:1, 11-18.

G. Hu, et al., Optically Active (aR)- and (aS)-Linear and Vaulted Biaryl Ligands: Deracemization versus Oxidative Dimerization, Journal of the American Chemical Society (2009), 131, 14355-14364.

V. Kalyvas and J. McIntyre, Thermotropic Liquid Crystal Behavior in Some Aromatic Esteramides, Molecular Crystals and Liquid Crystals (1982), 80, 105-118.

E. Marvell, et al., Photocyclization of 2-Methoxy-4,5-dimethylstilbene, Journal of Organic Chemistry (1977), 42:23, 3783-3784.

E. Montbach, et al., Novel Flexible Reflex Displays, Proceedings of the SPIE (2009), 7232, 723203-1-723203-8.

R. Redic and G. Schuster, Chirochromic triggers: 3,3'-Distributed-2,2'-binaphthalene-1,1'-diols and 2-methylindoline derived phosphoramidates, Journal of Photochemistry and Photobiology A: Chemistry (2006) 179, 66-74.

G. Spada and G. Proni, The Nematic Liquid Crystal Phase as a Probe of the Molecular Shape Helicity, Enantiomer (1998) 3, 301-314.

Wu, et al., Synthesis and Lyotropic Behavior of Mesogen-Linked Cellulose Acetates, Journal of Applied Polymer Science (2004), 92, 2693-2697.

M. Zhang and G. Schuster, Chirochromism-Photochromism by Epimerization: Search for a Liquid Crystal Phototrigger, Journal of the American Chemical Society (1994), 116, 4852-4857.

\* cited by examiner

2,2'-BINAPHTHALENE ESTER CHIRAL DOPANTS FOR CHOLESTERIC LIQUID CRYSTAL DISPLAYS

BACKGROUND OF THE INVENTION

Chiral nematic, also known as cholesteric, liquid crystalline materials are useful in a variety of applications including various liquid crystal (e.g.: LC) displays, electronic writers or tablets, electronic skins, reflective films, optical filters, polarizers, paints, and inks, among others. Methods for preparing such materials are well established. See for example: G. Gottarelli and G. Spada, *Mol. Cyst. Liq. Cys.*, 123, 377 (1985); G. Spada and G. Proni, *Enantiomer*, 3, 301 (1998); E. Montbach, et al, *Proceedings of SPIE*, 7232, 723203, (2009). However, improvement is still needed. While early uses of chiral nematic compositions relied upon mixtures composed mostly of chiral components, more recently such materials are composed of nematic liquid crystal (LC) mixtures combined with small amounts of chiral dopants. In such new compositions the properties of the nematic host material, for example: viscosity, birefringence, electrical anisotropy, and magnetic anisotropy among others, are tailored to the desired usage by altering the chemical composition of the nematic mixture and then a chiral dopant is incorporated to induce helical twisting so as to provide the desired chiral nematic pitch. It is apparent that the properties of this chiral nematic composition are therefore a combination of the properties of the nematic host plus those of the dopant.

Chiral nematic liquid crystals can be formulated to reflect various wavelengths of incident electromagnetic radiation, and it is well understood that the reflected light is circularly polarized, depending upon the sense of chirality of the helical pitch. Thus a chiral nematic displaying a right-handed helical mesostructure will reflect right-handed incident light. For many applications it is useful to be able to reflect both right-handed and left-handed sense of circularly polarized light, for example, in a vertically layered structure. It is further well known that enantiomers of a chiral dopant structure induce the opposite polarity of helical rotation and, therefore, afford oppositely polarized light reflections. For this reason the preparation of enantiomeric pairs of dopants for use in separate light modulating layers can be particularly useful.

For some applications it is desirable to have liquid crystal mixtures that exhibit a strong helical twist and thus a short pitch length. A short pitch can be achieved by using high amounts of dopant or by using a dopant with a high helical twisting power. However, using chiral dopants in high amounts can negatively affect the properties of the liquid crystalline host mixture, for example; the dielectric anisotropy, the viscosity, and the driving voltage or the switching times among others. In liquid crystalline mixtures that are used in selectively reflecting cholesteric displays, the pitch has to be selected such that the maximum of the wavelength reflected by the cholesteric helix is in the range of visible light. Another possible application is polymer films with a chiral liquid crystalline phase for optical elements, such as cholesteric broadband polarizers or chiral liquid crystalline retardation films.

Such liquid crystalline materials can be used for the preparation of polymer films with a chiral liquid crystalline phase, for active and passive optical elements or color filters and for liquid crystal displays, for example STN, TN, AMD-TN, temperature compensation, guest-host or phase change displays, or polymer free or polymer stabilized cholesteric texture (PFCT, PSCT) displays. Such liquid crystal displays can include a chiral dopant in a liquid crystalline medium and a polymer film with a chiral liquid crystalline phase obtainable by (co)polymerizing a liquid crystalline material containing a chiral dopant and a polymerizable mesogenic compound.

1,1'-Binaphthalene chiral dopants have been long known and well studied. They are reported to display useful helical twisting power when they are used as dopants in nematic liquid crystals, see for example: Hoechst U.S. Pat. No. 4,826,620 (May 2, 1989), Mitsubishi Gas Chemical Co. U.S. Pat. No. 6,699,532 (Mar. 2, 2004), and Chisso Corp. U.S. Pat. No. 7,413,782 (Aug. 19, 2008). A comparison of 1,1'-binaphthalenes with other chiral dopant compounds is reported by G. Solladie and R. Zimmermann in *Journal of the American Chemical Society*, 1983, 105, 7318-7321 and by G. Spada and G. Proni in *Enantiomer*, 1998, 3, 301-314, and also by M. Bauer, C. Boeffel, F. Kuschel, and H. Zaschke in *Journal of the SID*, 2006, 14/9, 805-812. The 1,1'-binaphthalene compounds, also known as BINOL compounds, are termed atropisomer-based dopants since they possess a chiral plane or axis. The helical twisting power of 1,1'-binaphthalene compounds is largely dependent upon the dihedral angle of the two naphthalene rings as reported in the review by R. Eelkema and B. L. Fering a: *Org. Biomol. Chem.*, 2006, 4, 3729-3745. The dihedral angle of 1,1'-binaphthalene chiral dopants is dependent upon the substituents. Thus, it has been recognized that minor changes in the substituents of BINOL compounds can exhibit large molecular changes in cisoid and transoid conformations resulting in highly variable helical twisting powers.

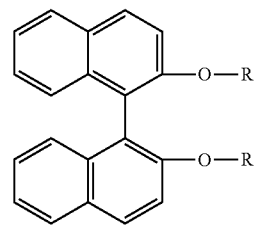

1,1'-binapthalene compounds

However, 2,2'-binaphthalene compound have received much less study in liquid crystal materials. The 4,4'-dialkoxy-2,2'-binaphthalene-1,1'-di(meth)acrylate compounds have recently been described to have high refractive index as reported by Kawasaki Kasei Chemicals in JP2011256119 (Dec. 22, 2014 Gossypol, a substituted 2,2'-binaphthalene, has been described for use in a multi-parameter rapid food contamination analyzer containing a liquid crystal display device as reported by Changchun Jilin University-Little Swan Instruments Co. in CN1900694 (Jan. 24, 2007). The 3,3'-disubstituted-2,2'-binaphthalene-1,1'-diols and 2-methylindoline derived phosphoramidates have been studied as chirochromic triggers as reported by R, Redic and G. B. Schuster in *Photochem. and Photobio. A: Chem.*, 2006, 179, 66-74. In particular, 2,2'-binaphthalene compounds with 1,1'-diarylcarboxyloxy substitution have previously been unreported.

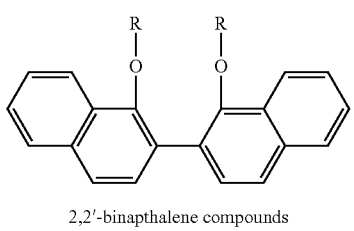

2,2'-binapthalene compounds

Thus there is a considerable demand for new chiral dopants with a high helical twisting power which can be easily synthesized in individual enantiomeric pairs, which can be used in low amounts, show improved temperature stability of the cholesteric pitch for utilizing a temperature invariant reflection wavelength and do not affect the properties of the liquid crystal host mixture.

We have found new inventive chiral dopants of the 2,2'-binaphthalene esters which provide these properties, can be prepared easily, have uniformly high helical twisting power, and do not have the disadvantages of the dopants of the state of the art as discussed above.

BRIEF DESCRIPTION OF THE INVENTION

We have found that certain 2,2'-binaphthalene compounds represented by the following Structure 1 are useful as a source of chiral dopants. In particular, the enantiomerically enriched form of such compounds, including the substantially enantiomerically pure form, introduced into nematic compositions, afford useful chiral nematic mixtures.

Structure 1

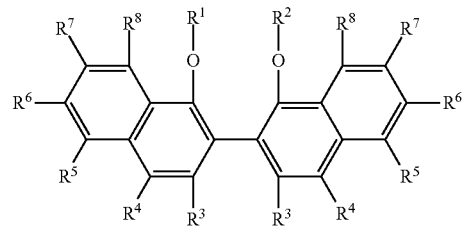

In a first embodiment a liquid crystal composition comprises a chiral dopant compound represented by the Structure 1 comprising two naphthalene rings connected at the 2,2' position of each naphthalene nucleus and the substituents at the 1,1' positions each contain an oxygen attached to the naphthalene ring. It is understood that the substituents on the naphthalene rings may not necessarily be symmetrically attached as long as one pair of oxygen containing substituents are in the 1,1' positions. In Structure 1, R1 and R2 are independently hydrogen, —(C=O)R9, —(C=O)R10, alkyl, aryl, alkaryl, alkenyl, cycloalkyl, alkoxyaryl or heterocyclic all either substituted or unsubstituted, or combine to form a carbocyclic or heterocyclic ring; R3 is hydrogen, halogen, cyano, alkoxy, NHCOR9, NHSO2R9, COOR9, OCOR9, aryl, alkyl, alkenyl, cycloalkyl, or heterocyclic all either substituted or unsubstituted; R4 is hydrogen, alkyl, aryl, alkenyl, cycloalkyl, or heterocyclic all either substituted or unsubstituted; R5, R6, R7, and R8 are independently hydrogen, halogen, cyano, alkoxy, NHCOR9, NHSO2R9, COOR9, OCOR9, aryl, alkyl, alkenyl, cycloalkyl, alkoxyaryl or heterocyclic all either substituted or unsubstituted, or combine with each other, or R5 can combine with R4, to form a carbocyclic or heterocyclic ring; and R9 and R10 are independently alkyl, alkoxy, aryl, naphthyl, styryl, alkenyl, cycloalkyl, alkoxyaryl, cycloalkoxy, or heterocyclic all either substituted or unsubstituted, or combine to form a carbocyclic or heterocyclic ring.

Referring to a more specific feature of the compound of Structure 1, R9 and R10 are aryl either substituted or unsubstituted as defined by: —R9 or —R10=—(Y—K)$_p$—Z: wherein K is a single bond or double bond or bivalent linking selected from the group consisting of: —C(=O)O—; —O(C=O)—; —CH2CH2-; —CH=CH—; —C≡C—; —OCH2-; —CH2O—; —N=CH—; —CH=N—; —O(C=O)O—; —C≡C—C≡C—; —COCH=CH—; —CH=CHCO—; —O—; —S—; and SO2; as long as oxygen atoms are not linked directly to one another; wherein Y and Z independently are optionally selected from the group consisting of: 1,4-phenylene in which, in addition, one or more methylene may be replaced by —N=; 1,4-cyclohexyl in which, in addition, one or more non-adjacent methylene units may be replaced by O or S; 1,4-cyclohexylene; 1,4-bicyclo[2.2.2]octylene; piperidine-1,4-diyl; decahydronaphthalene-1,6-diyl; and 1,2,3,4-tetrahydronaphthalene-1,6-diyl; wherein each of the Y or Z groups may be unsubstituted or mono-substituted or poly-substituted with halogen, cyano, isocyanato, or nitro groups, or alkyl, alkoxyl, or alkanoyl groups bearing 1-12 carbons where one or more hydrogens may be replaced with chlorine or fluorine; and wherein p=0, 1, 2, 3, 4.

In a second embodiment a liquid crystal composition comprises a chiral dopant compound represented by the following Structure 2:

Structure 2

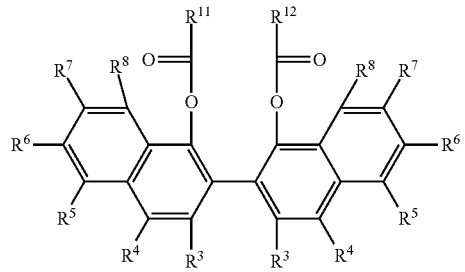

wherein R3, R4, R5, R6, R7, and R8 are as defined above, R9 is independently alkyl, aryl, alkenyl, cycloalkyl, alkoxyaryl or heterocyclic all either substituted or unsubstituted, and R11 and R12 are independently alkyl, alkoxy, aryl, naphthyl, styryl, alkenyl, cycloalkyl, cycloalkyloxy, alkoxyaryl or heterocyclic all either substituted or unsubstituted, or combine to form a carbocyclic or heterocyclic ring; but the two oxygen containing substituents at 1 and 1' are each substituted with a carbonyl containing substituent.

In a third embodiment a liquid crystal composition comprises a chiral dopant compound represented by the following Structure 3:

Structure 3

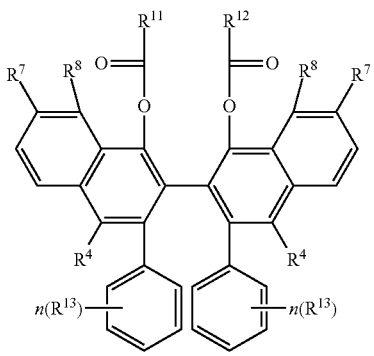

wherein R4, R7, R8, R9, R11 and R12 are as defined above, and

R13 is hydrogen, halogen, cyano, alkoxy, NHCOR9, NHSO2R9, COOR9, OCOR9, aryl, alkyl, alkenyl, cycloalkyl, or heterocyclic all either substituted or unsubstituted; n is 1-5.

In a fourth embodiment a liquid crystal composition comprises a chiral dopant compound represented by the following Structure 4:

Structure 4

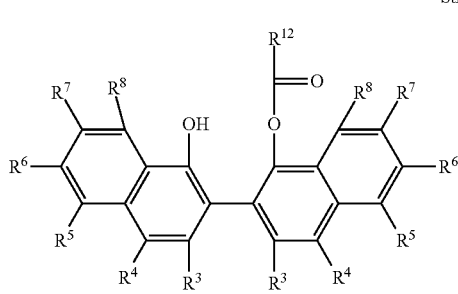

wherein R3, R4, R5, R6, R7, R8, R9, R10 and R12 are as defined above.

More specific features that may apply to the liquid crystal compositions including the chiral dopant compounds of Structures 1, 2, 3 or 4 will now be addressed. The liquid crystal composition may include an enantiomerically excess of one enantiomer of the chiral dopant compound. R3 can be an aryl group either substituted or unsubstituted in the compounds of Structures 1, 2 or 4. A liquid crystal composition can comprise the chiral dopant admixed with a liquid crystal material, wherein the chiral dopant compound is optionally in a polymerized form. The liquid crystal composition can comprise a polymer binder in which domains of the liquid crystal material are dispersed. The liquid crystal composition can comprise at least one of a catalyst, a sensitizer, a stabilizer, a co-reacting monomer, or a surface-active compound. The liquid crystalline composition can be STN, TN, chiral nematic, or ferroelectric. The liquid crystalline composition can be chiral nematic. A liquid crystal display, electronic writer/tablet, electronic skin, optical element, or color filter can comprise the liquid crystal composition. The display can be selected from the group consisting of a STN, TN, TFT-TN, guest-host, phase change, polymer free cholesteric texture, polymer stabilized cholesteric texture and ferroelectric display.

Regarding another specific feature that can apply to the compounds of Structures 2, 3 or 4 above, R11 and R12 are aryl either substituted or unsubstituted as defined by: —R11 or —R12 =—(Y—K)$_p$—Z: wherein K is a single bond or double bond or bivalent linking selected from the group consisting of: —C(=O)O—; —O(C=O)—; —CH2CH2-; —CH=CH—; —C≡C—; —OCH2-; —CH2O—; —N=CH—; —CH=N—; —O(C=O)O—; —C≡C—C≡C—; —COCH=CH—; —CH=CHCO—; —O—; —S—; and SO2; as long as oxygen atoms are not linked directly to one another; wherein Y and Z independently are optionally selected from the group consisting of: 1,4-phenylene in which, in addition, one or more methylene may be replaced by —N=; 1,4-cyclohexyl in which, in addition, one or more non-adjacent methylene units may be replaced by O or S; 1,4-cyclohexylene; 1,4-bicyclo[2.2.2]octylene; piperidine-1,4-diyl; decahydronaphthalene-1,6-diyl; and 1,2,3,4-tetrahydronaphthalene-1,6-diyl; wherein each of the Y or Z groups may be unsubstituted or mono-substituted or poly-substituted with halogen, cyano, isocyanato, or nitro groups, or alkyl, alkoxyl, or alkanoyl groups bearing 1-12 carbons where one or more hydrogens may be replaced with chlorine or fluorine; and wherein p=0, 1, 2, 3, 4.

Many additional features, advantages and a fuller understanding of the invention will be had from the Detailed Description that follows. It should be understood that the above Brief Description describes the invention in broad terms while the following Detailed Description describes the invention more narrowly and presents specific embodiments that should not be construed as necessary limitations of the broad invention as defined in the claims.

DETAILED DESCRIPTION OF THE INVENTION

We have found that certain 2,2'-binaphthalene compounds represented by the following Structures 1-4 below are useful as a source of chiral dopants. In particular, the enantiomerically enriched form of such compounds, including the substantially enantiomerically pure form, introduced into nematic compositions, afford useful chiral nematic mixtures. The invention features liquid crystal compositions comprising the chiral dopants of Structures 1-4 below.

Structure 1

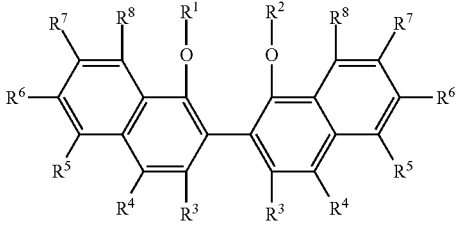

The first embodiment features the chiral dopant of Structure 1. As evident compounds of Structure 1 comprise two naphthalene rings connected at the 2,2' position of each naphthalene nucleus and the substituents at the 1,1' positions each contain an oxygen attached to the naphthalene ring. It is understood that the substituents on the naphthalene rings may not necessarily be symmetrically attached as long as one pair of oxygen containing substituents are in the 1,1' positions. In Structure 1, R1 and R2 are independently hydrogen, —(C=O)R9, —(C=O)R10, alkyl, aryl, alkenyl, cycloalkyl, alkoxyaryl or heterocyclic all either substituted or unsubstituted, or combine to form a carbocyclic or heterocyclic ring; R3 is hydrogen, halogen, cyano, alkoxy, NHCOR9, NHSO2R9, COOR9, OCOR9, aryl, alkyl, alkenyl, cycloalkyl, or heterocyclic all either substituted or unsubstituted; R4 is hydrogen, alkyl, aryl, alkenyl, cycloalkyl, or heterocyclic all either substituted or unsubstituted; R5, R6, R7, and R8 are independently hydrogen, halogen, cyano, alkoxy, NHCOR9, NHSO2R9, COOR9, OCOR9, aryl, alkyl, alkenyl, cycloalkyl, alkoxyaryl or heterocyclic all either substituted or unsubstituted, or combine with each other, or R5 can combine with R4, to form a carbocyclic or heterocyclic ring; and R9 and R10 are independently alkyl, alkoxy, aryl, naphthyl, styryl, alkenyl, cycloalkyl, alkoxyaryl, cycloalkoxy, or heterocyclic all either substituted or unsubstituted, or combine to form a carbocyclic or heterocyclic ring.

The chiral dopant of the second embodiment is represented by the following Structure 2:

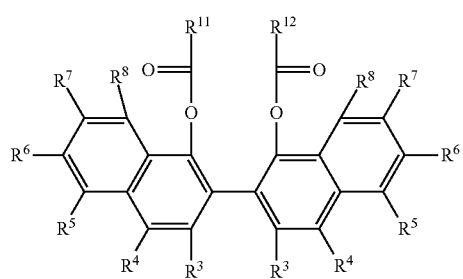

Structure 2 wherein R3, R4, R5, R6, R7, and R8 are as defined above, R9 is independently alkyl, aryl, alkenyl, cycloalkyl, alkoxyaryl or heterocyclic all either substituted or unsubstituted, and R11 and R12 are independently alkyl, alkoxy, aryl, naphthyl, styryl, alkenyl, cycloalkyl, cycloalkyloxy, alkoxyaryl or heterocyclic all either substituted or unsubstituted, or combine to form a carbocyclic or heterocyclic ring; but the two oxygen containing substituents at 1 and 1' are each substituted with a carbonyl containing substituent.

The chiral dopant of the third embodiment is represented by the following Structure 3:

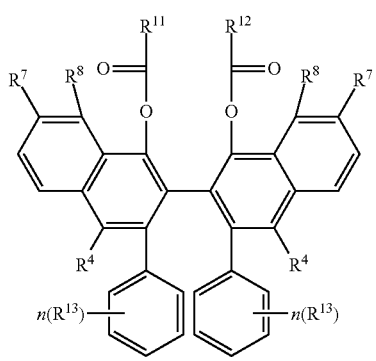

Structure 3 wherein R4, R7, R8, R9, R11 and R12 are as defined above, and

R13 is hydrogen, halogen, cyano, alkoxy, NHCOR9, NHSO2R9, COOR9, OCOR9, aryl, alkyl, alkenyl, cycloalkyl, or heterocyclic all either substituted or unsubstituted;

n is 1-5.

The chiral dopant of the fourth embodiment is represented by the following Structure 4:

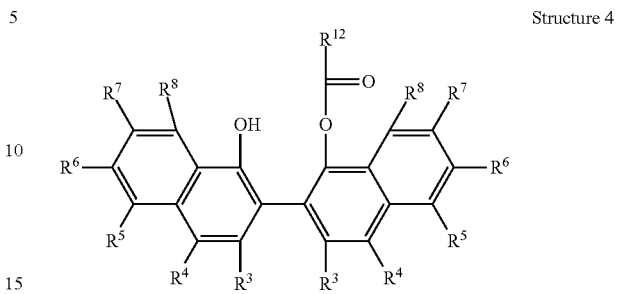

Structure 4 wherein R3, R4, R5, R6, R7, R8, R9 and R12 are as defined above.

In general, when reference in this application is made to a particular moiety group it is to be understood that such reference encompasses that moiety whether unsubstituted or substituted with one or more substituents (up to the maximum possible number). For example, "alkyl" or "alkyl group" refers to substituted or unsubstituted alkyl, while "benzene group" refers to a substituted or unsubstituted benzene (with up to six substituents), and "naphthalene group" refers to a substituted or unsubstituted naphthalene (with up to 8 substituents). Generally unless otherwise specifically stated, substituent groups usable on molecules herein include any groups, whether substituted or unsubstituted, which do not destroy properties necessary for mesophase utility. Examples of substituents on any of the mentioned groups can include known substituents, such as: chloro, fluoro, bromo, iodo, hydroxyl, alkoxy, particularly those of "lower alkyl" (that is, with 1 to 12 carbon atoms, for example, methoxy, ethoxy); substituted or unsubstituted alkyl, particularly lower alkyl (for example, methyl, trifluoromethyl); thioalkyl, particularly either of those with 1 to 12 carbon atoms, (for example, methylthio or ethylthio); substituted or unsubstituted alkenyl, preferably of 2 to 12 carbon atoms (for example, ethenyl, propenyl, or butenyl); substituted or unsubstituted aryl, particularly those having from 6 to 20 carbon atoms (for example, phenyl, naphthyl); substituted or unsubstituted cycloalkyl, particularly those having from 5 to 20 carbon atoms (for example, cyclopentyl, or cyclohexyl); and substituted or unsubstituted heteroaryl, particularly those having a 5 or 6-membered ring containing 1 to 3 heteroatoms selected from N, O, or S (for example, pyridyl, thienyl, furyl, pyrrolyl); acid or acid salt groups; such groups as hydroxyl, amino, alkylamino, cyano, nitro, carboxy, carboxylate, acyl, alkoxycarbonyl, aminocabonyl, sulfonamide, sulfamoyl, sulfo, sulfonate, or alkylammonium; and other groups known in the art. In particular, alkyl substituents may specifically include "lower alkyl" (that is, having 1-12 carbon atoms), for example, methyl, ethyl, and the like. Further, with regard to any alkyl group or alkylene group, it will be understood that these can be branched or unbranched and include ring structures.

The R1 and R2 group in Structure 1 is independently hydrogen or any substituent preferably having 1 to 24 carbon atoms, more preferably 2 to 18 carbon atoms. It is preferred to be aryl, alkyl, alkenyl, cycloalkyl, alkaryl, alkoxyaryl, or heterocyclic either substituted or unsubstituted, or combine to form a carbocyclic or heterocyclic ring. It is particularly preferred for the R1 and R2 group to contain a carbonyl and an aromatic or cycloalkyl ring, which may be the same or different, for example, a phenyl-containing group. It is most preferred that R1 and R2 contain a carbonyl and a substituent, R9 and R10, as defined by: R9, R10=—(Y—K)$_p$—Z: wherein K is a single bond or double bond, e.g. —(Y)$_p$—Z or bivalent linking selected from the group consisting of: —C(=O)O—; —O(C=O)—; —CH2CH2-; —CH=CH—; —C≡C—; —OCH2-; —CH2O—; —N=CH—; —CH=N—; —O(C=O)O—; —C=C—C=C—; —COCH=CH—; —CH=CHCO—; —O—; —S—; and SO2; as long as oxygen atoms are not linked directly to one another; wherein Y and Z independently are optionally selected from the group consisting of 1,4-phenylene in which, in addition, one or more methylene may be replaced by —N=; 1,4-cyclohexyl in which, in addition, one or more non-adjacent methylene units may be replaced by O or S; 1,4-cyclohexylene; 1,4-bicyclo[2.2.2]octylene; piperidine-1,4-diyl; decahydronaphthalene-1,6-diyl; and 1,2,3,4-tetrahydronaphthalene-1,6-diyl; wherein each of the Y or Z groups may be unsubstituted or mono-substituted or poly-substituted with halogen, cyano, isocyanato, or nitro groups, or alkyl, alkoxyl, or alkanoyl groups bearing 1-12 carbons where one or more hydrogens may be replaced with chlorine or fluorine; and wherein p=0, 1, 2, 3, 4. As indicated above, R1 and R2 in Structure 1 can also be connected to form a carbocyclic or heterocyclic ring. In one preferred embodiment R1 is —(C=O)R9 and R2 is hydrogen or —(C=O)R10. In one highly preferred embodiment R1 is —(C=O)R9 and R2 is —(C=O)R10.

The R3 group in Structure 1, Structure 2 or Structure 4 can independently be any substituent. It is preferred to be an oxygen-containing organic substituent and/or a carbon containing substituent. Preferred oxygen-containing substituents include alkoxy, aryloxy, carboalkyl (—C(=O)R), carboaryl (O—C(=O)OAr), carboalkoxy (—C(=O)OR), carboaryloxy (O—C(=O)OAr) either substituted or unsubstituted. Preferred carbon containing substituents include alkyl groups of about 1-20 carbons, cycloalkyl groups of about 1-20 carbons, aryl groups of about 6-20 carbons, alkaryl groups of about 6-20 carbons, and heterocyclic groups having at least one heteroatom and 2-20 carbons; all either substituted or unsubstituted, as long as oxygen atoms are not linked directly to one another. Other preferred oxygen-containing organic substituents include carboalkoxy (C—C(=O)OR), carboaryloxy (C—C(=O)OAr), aryl or alkyl ketones (C—C(=O)R) or (C—C(=O)Ar), all either substituted or unsubstituted. Other suitable R3 substituents include but are not limited to halogens; cyano (—CN); hydroxyl, amino, alkylamino, nitro, carboxy, aminocarbonyl, sulfonamide, sulfamoyl, sulfo, sulfonate, or alkylammonium; as well as siloxane residue or polymerizable groups. The R4 group in Structures 1, 2, 3 or 4 is hydrogen, alkyl, aryl, alkenyl, cycloalkyl, or heterocyclic all either substituted or unsubstituted; in particular the R4 group is not alkoxy, and does not combine with R3 to form a carbocyclic ring. In one preferred embodiment R3 is alkyl or aryl and R4 is hydrogen. In one highly preferred embodiment R3 is aryl and R4 is hydrogen.

The R5 and R6 group in Structure 1, Structure 2 or Structure 4 are independently hydrogen, halogen, cyano, alkoxy, NHCOR9, NHSO2R9, COOR9, OCOR9, aryl, alkyl, alkenyl, cycloalkyl, alkoxyaryl or heterocyclic all either substituted or unsubstituted, or combine with each other to form a carbocyclic or heterocyclic ring, or R5 can combine with R4 to form a carbocyclic or heterocyclic ring. In one highly preferred embodiment R5 and R6 are hydrogen.

The R7 and R8 group in Structures 1, 2, 3 or 4 are independently a hydrogen, halogen, cyano, alkoxy, NHCOR9, NHSO2R9, COOR9, OCOR9, aryl, alkyl, alkenyl, cycloalkyl, alkoxyaryl or heterocyclic all either substituted or unsubstituted, or combine with each other to form a carbocyclic or heterocyclic ring. In one preferred embodiment R7 and R8 combine to form a carbocyclic aryl ring, or are hydrogen. In one highly preferred embodiment R7 and R8 are hydrogen.

The R11 and R12 groups in Structure 2 and Structure 3 and the R12 group in Structure 4 are independently aryl, naphthyl, styryl, alkyl, alkoxy, alkenyl, cycloalkyl, cycloalkyloxy, alkoxyaryl or heterocyclic all either substituted or unsubstituted, or R11 and R12 may combine to form a carbocyclic or heterocyclic ring. In one preferred embodiment R11 and R12 are independently substituted aryl or cycloalkyl. In one highly preferred embodiment R11 and R12 are independently substituted aryl.

The R13 in Structure 3 is hydrogen, halogen, cyano, alkoxy, NHCOR9, NHSO2R9, COOR9, OCOR9, aryl, alkyl, alkenyl, cycloalkyl, or heterocyclic all either substituted or unsubstituted. The n in Structure 3 is 1 to 5. In one preferred embodiment R13 is hydrogen or halogen and n is 1 to 5. In one highly preferred embodiment R13 is hydrogen and n is 5.

Some examples of compounds according to the present invention, which examples are merely illustrative and not intended to be limiting, are as follows:

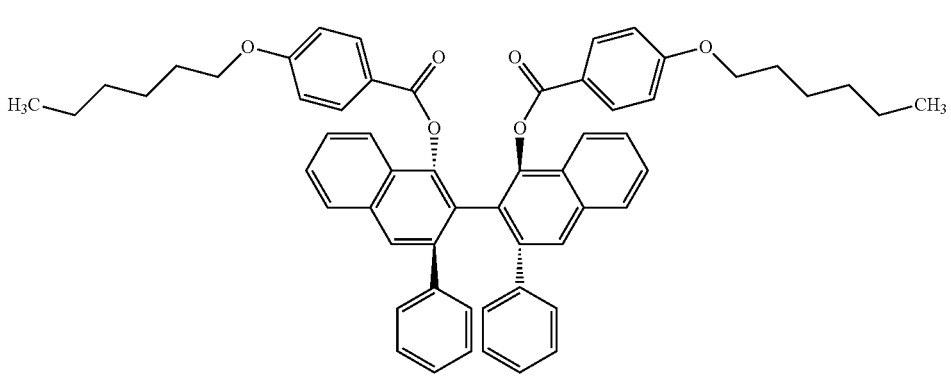

Inv-1

-continued
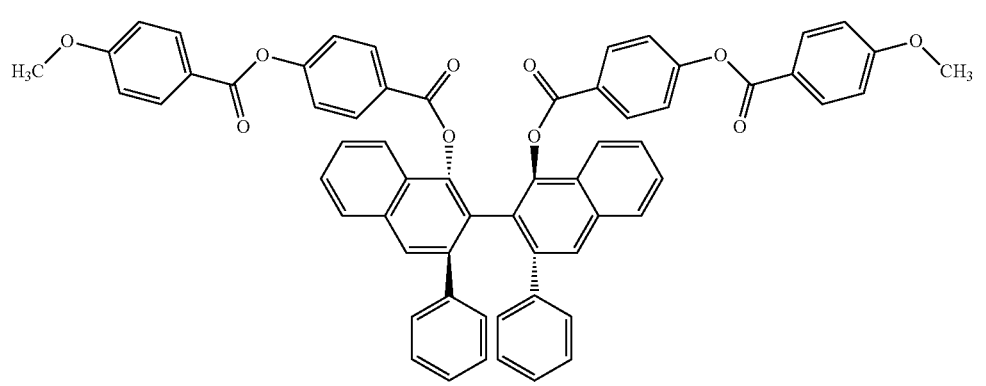
Inv-2
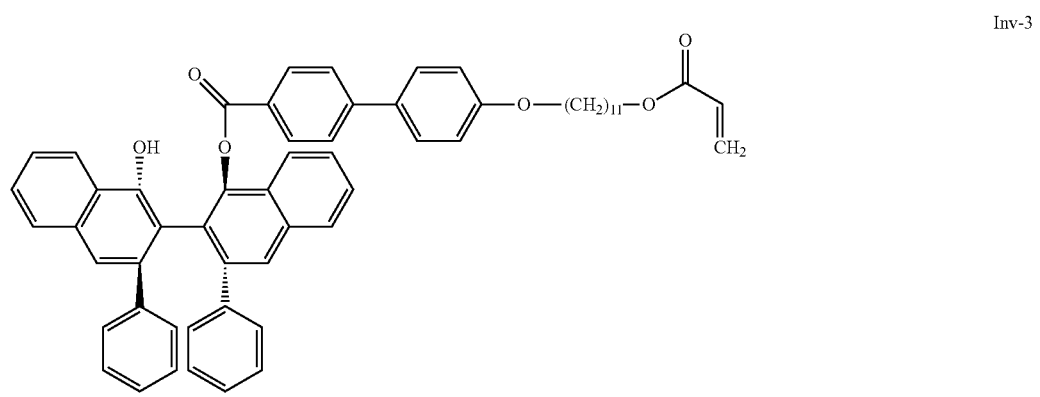
Inv-3
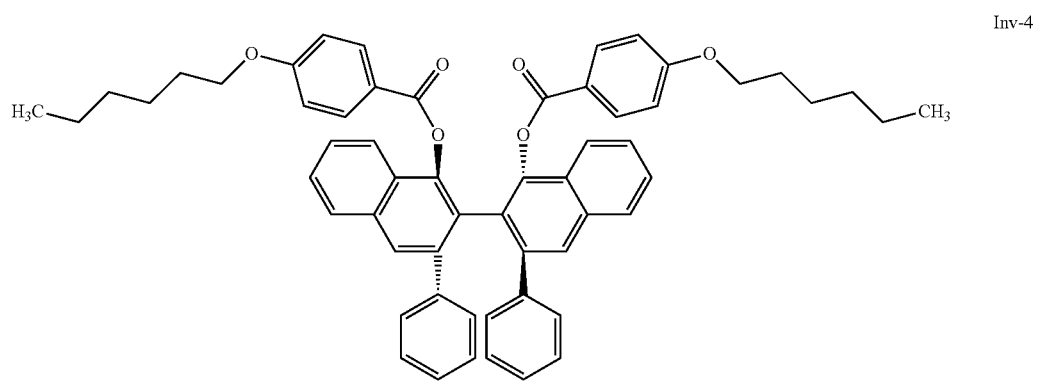
Inv-4
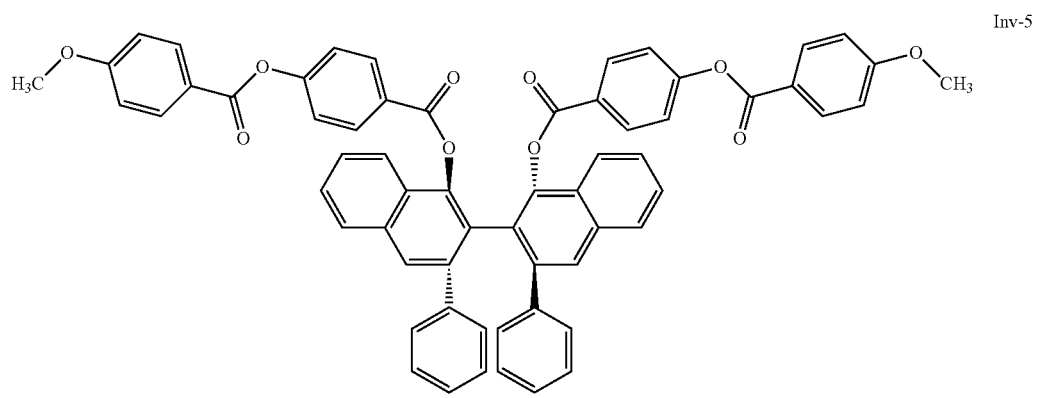
Inv-5

-continued
Inv-6
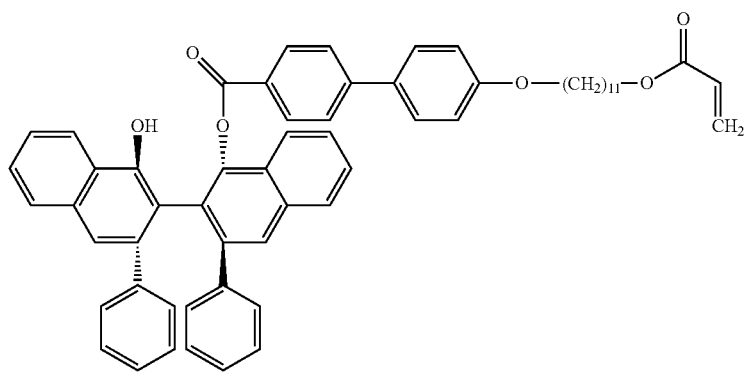
Inv-7
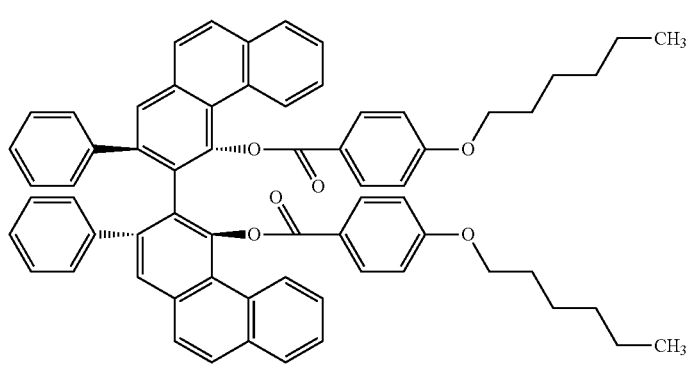
Inv-8
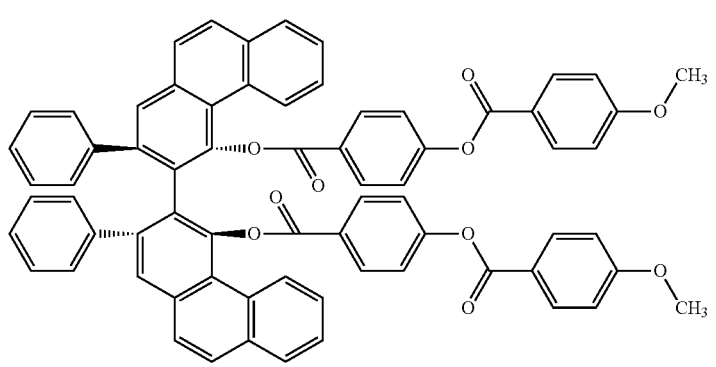
Inv-9
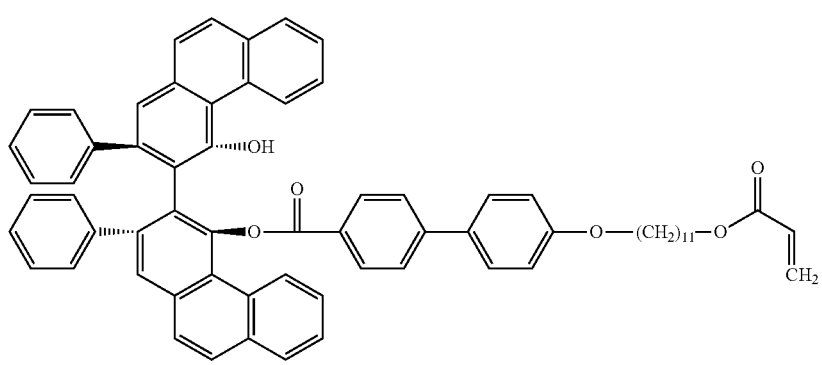

-continued
Inv-10
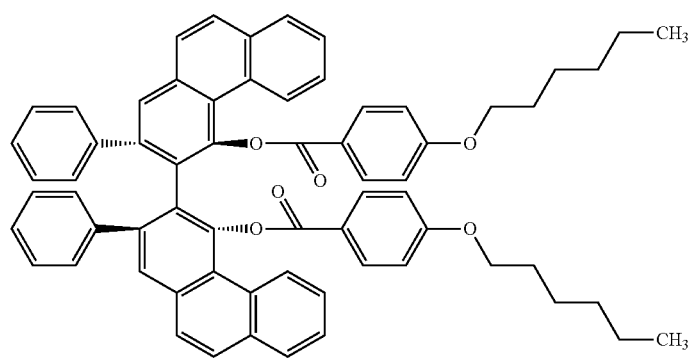
Inv-11
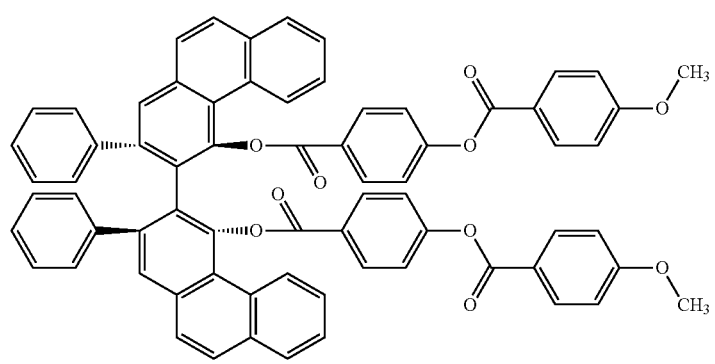
Inv-12
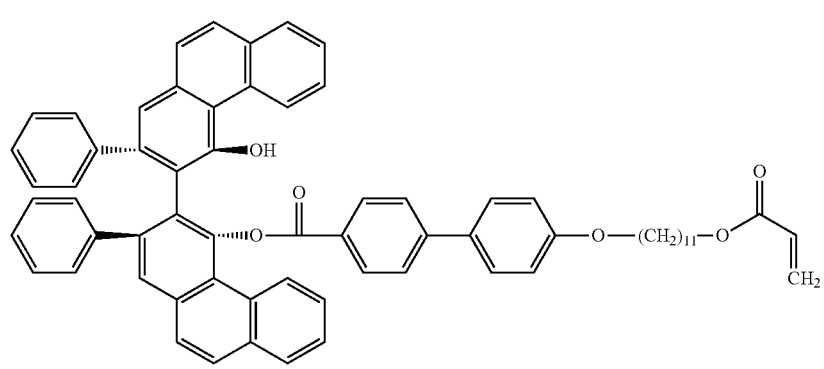
Inv-13
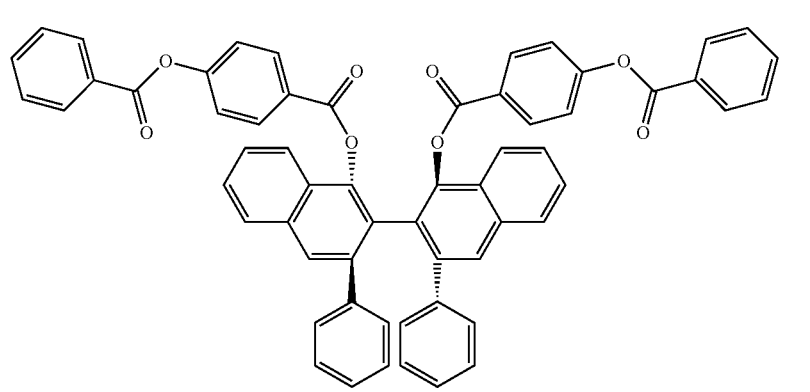

-continued
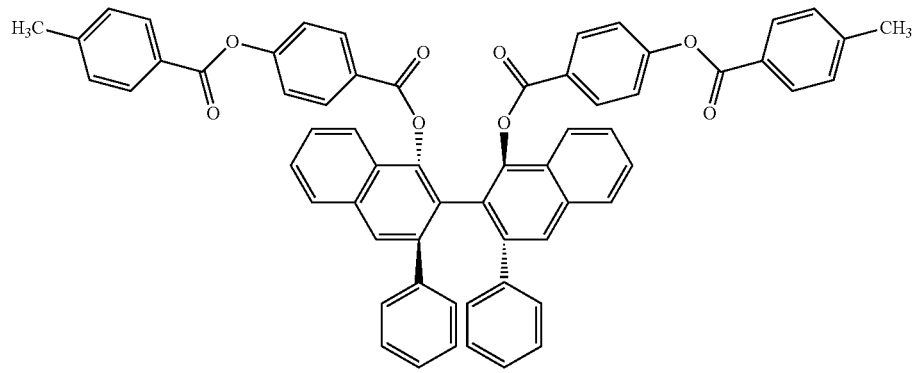
Inv-14
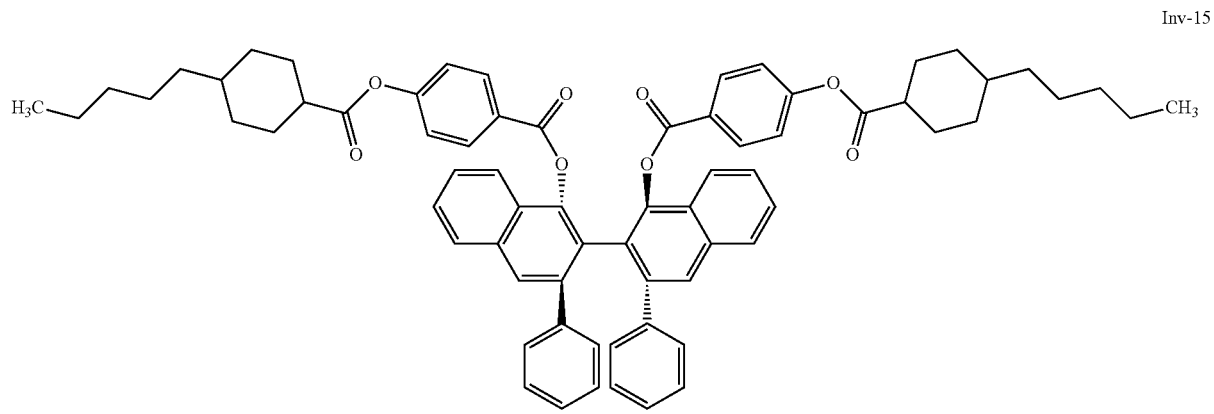
Inv-15
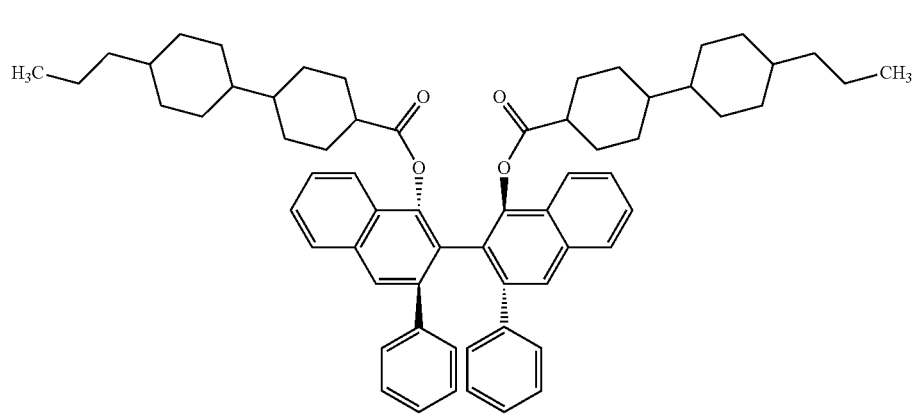
Inv-16
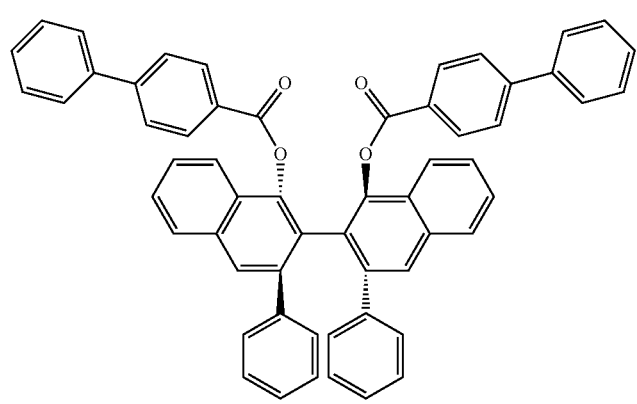
Inv-17

-continued
Inv-18
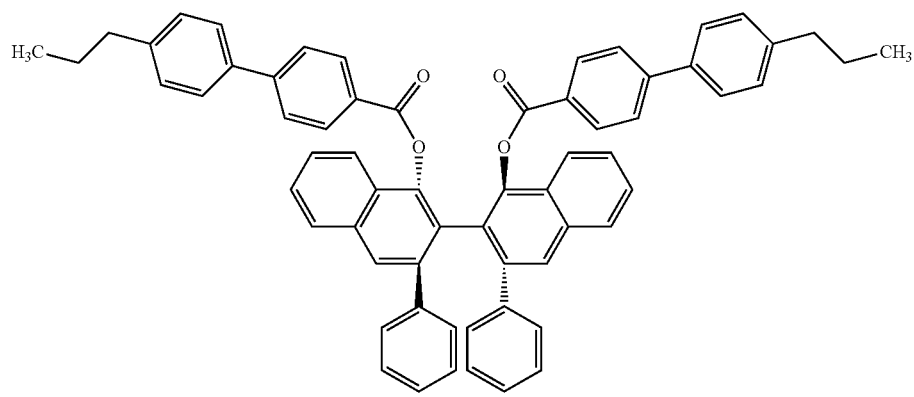
Inv-19
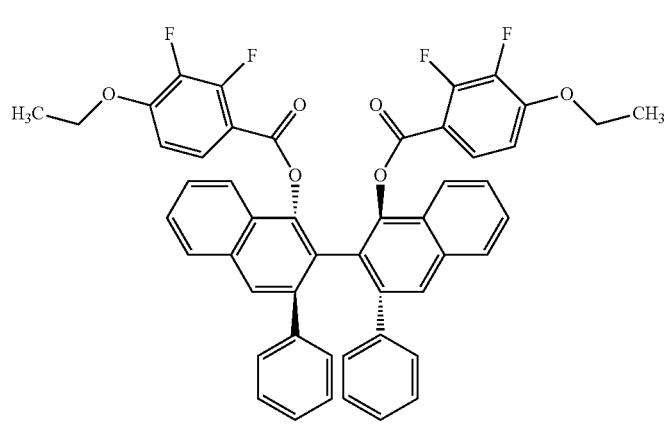
Inv-20
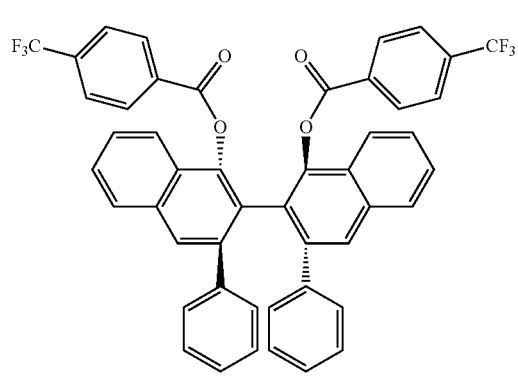
Inv-21
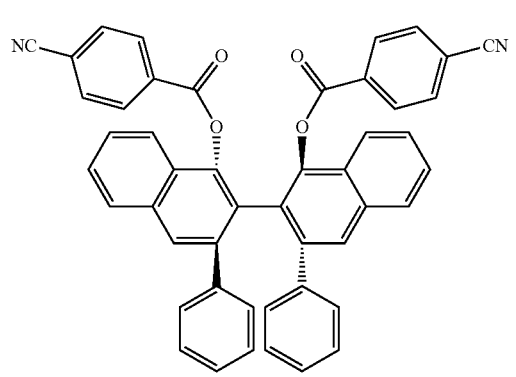

-continued
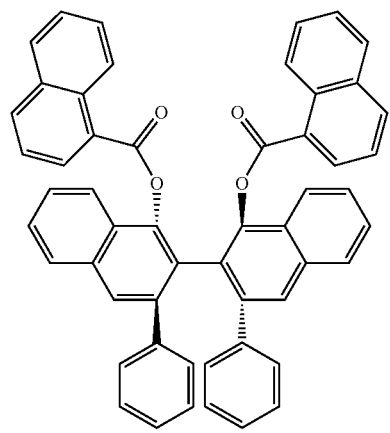
Inv-22
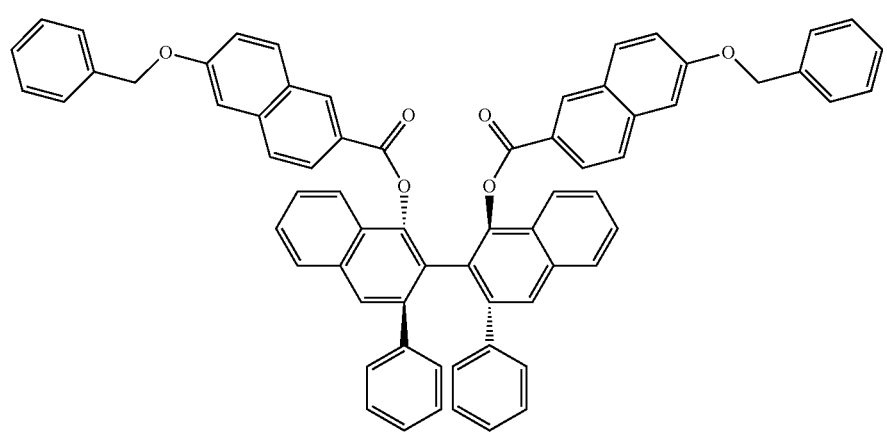
Inv-23
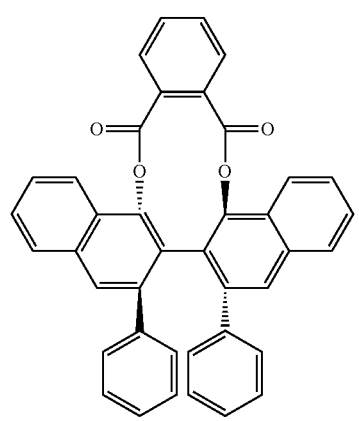
Inv-24
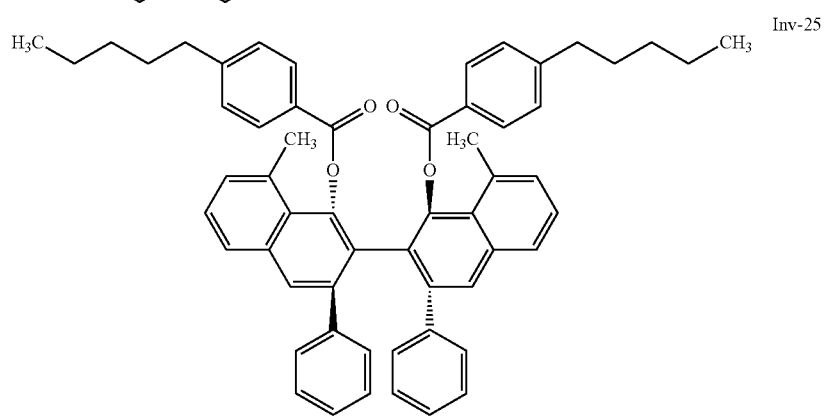
Inv-25

-continued
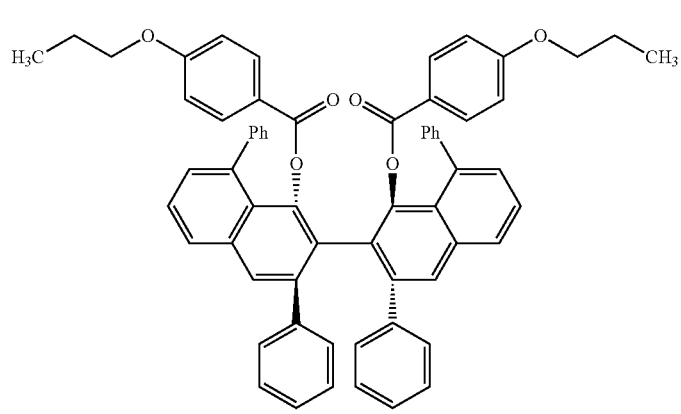
Inv-26
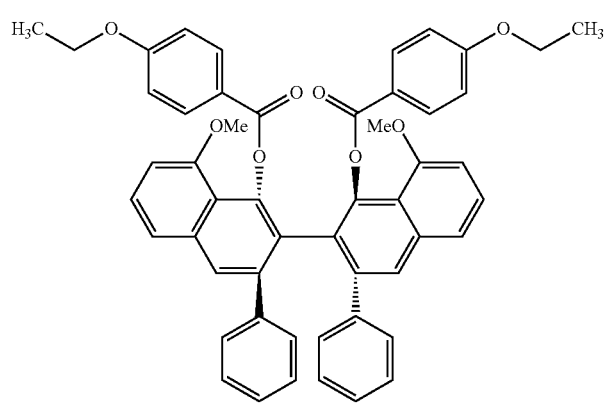
Inv-27
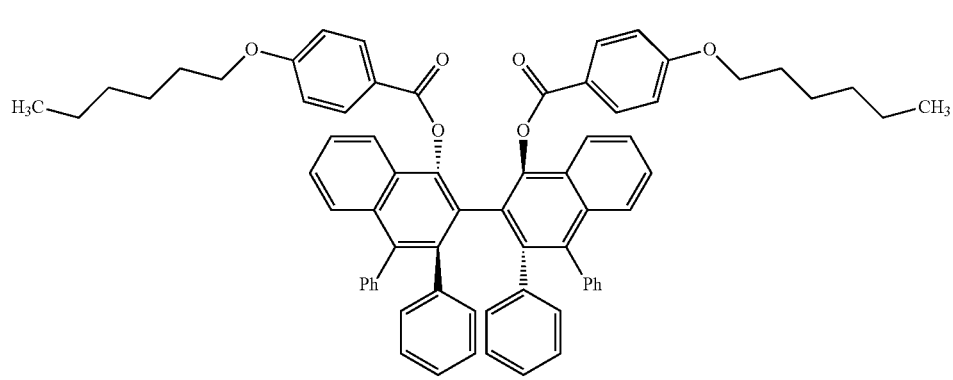
Inv-28
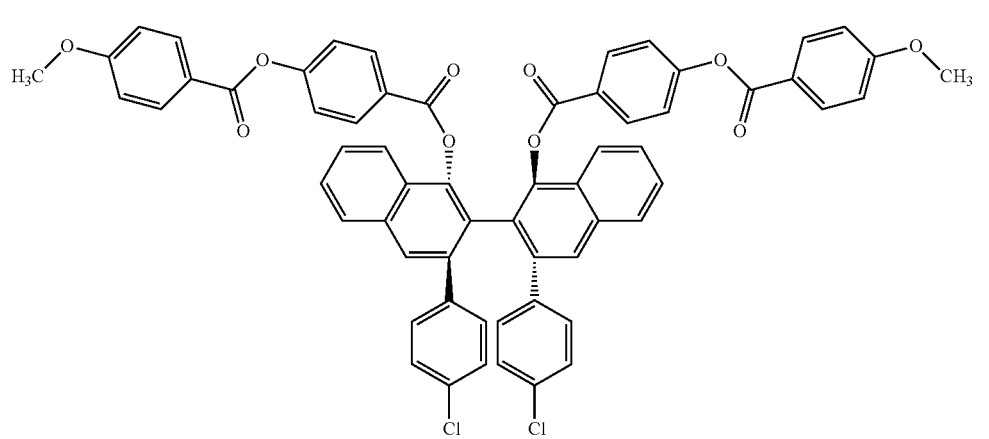
Inv-29

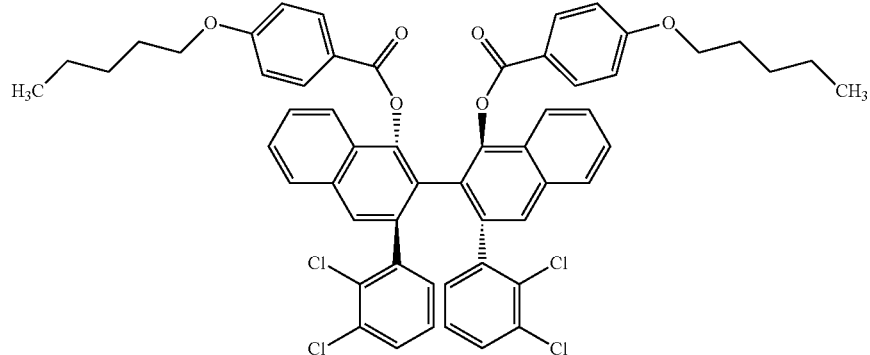
Inv-30
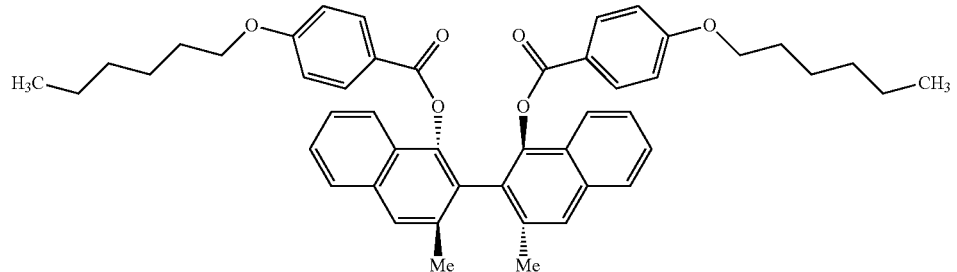
Inv-31
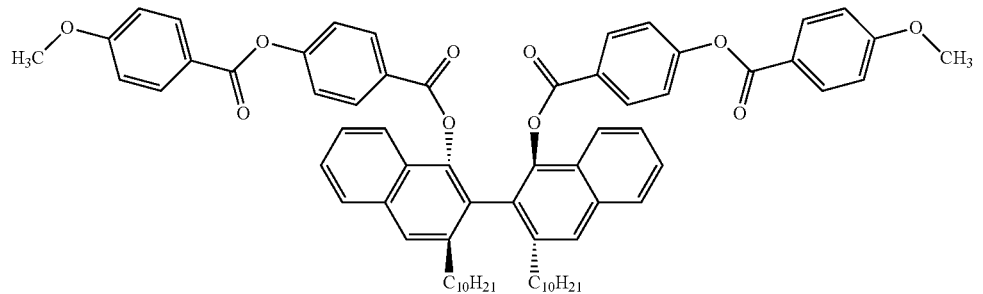
Inv-32
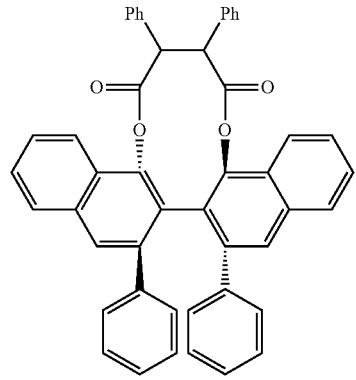
Inv-33

-continued
Inv-34
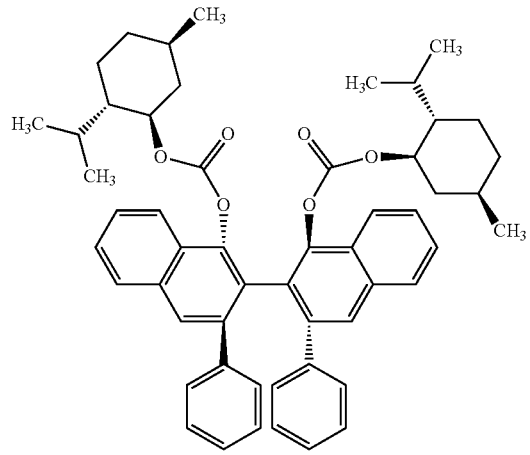
Inv-35
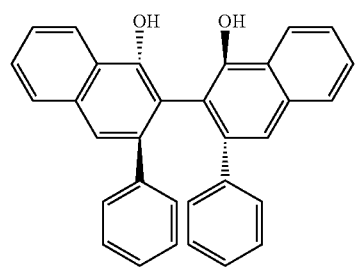
Inv-36
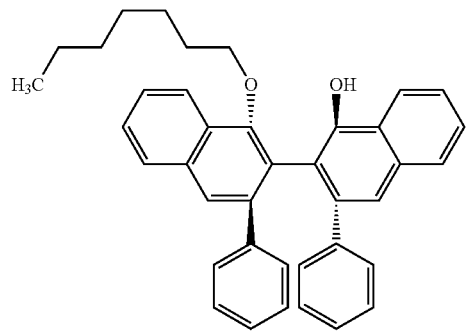
Inv-37
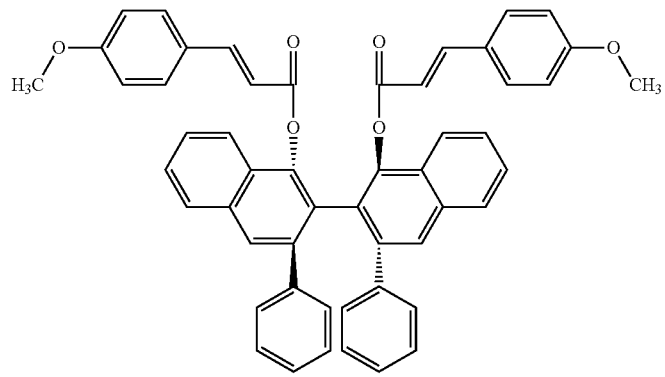

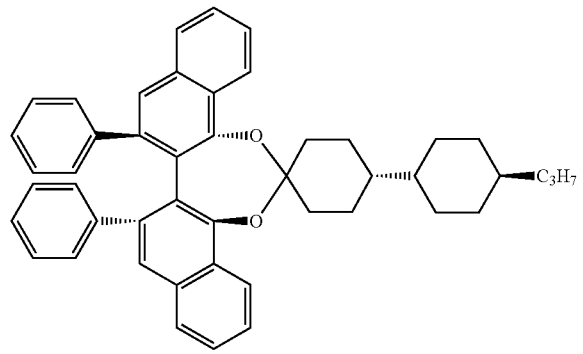
Inv-38
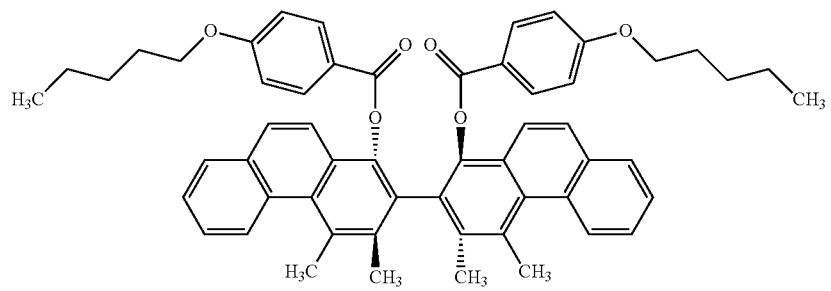
Inv-39
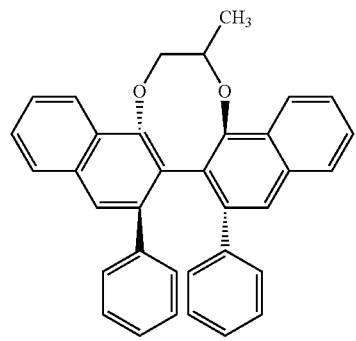
Inv-40
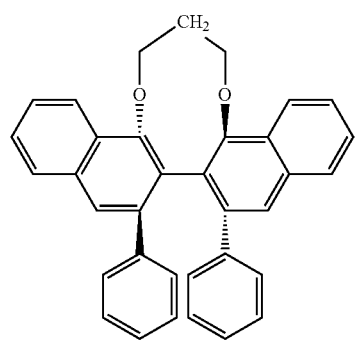
Inv-41

Inv-42
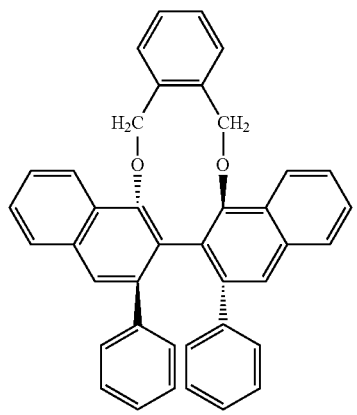
Inv-43
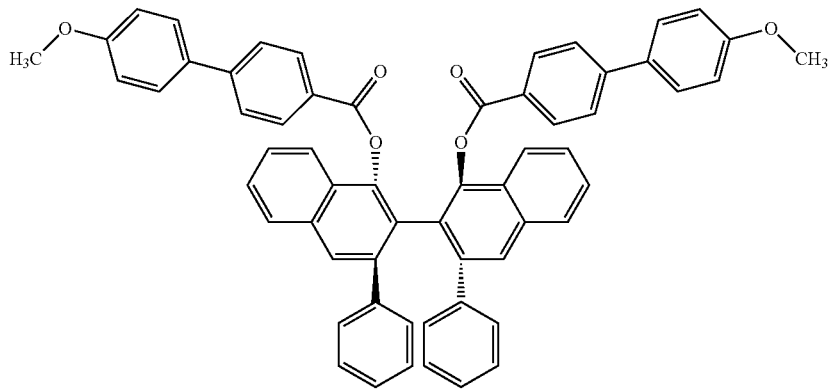
Inv-44
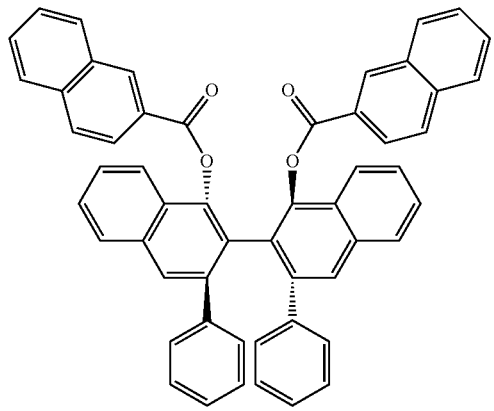
Inv-45
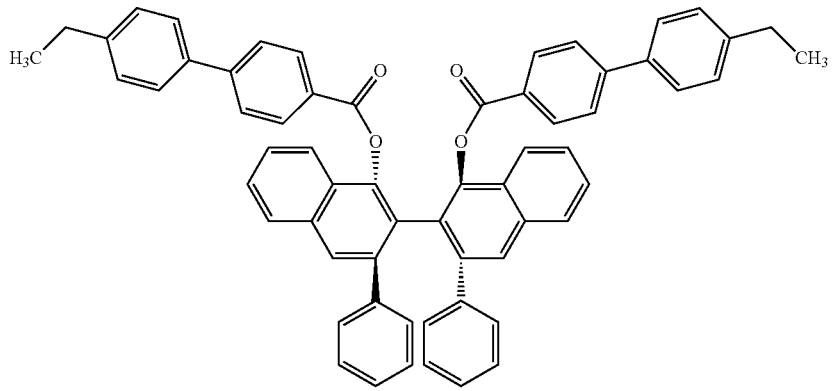

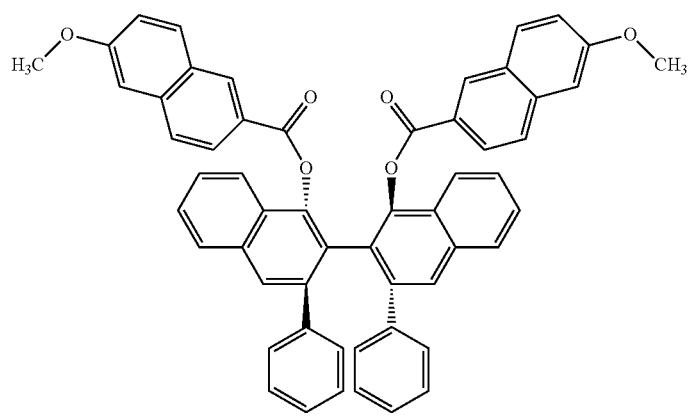

Inv-46

Chiral dopants of this invention can be readily prepared by those skilled in the art employing standard chemical transformations or by analogy to the reaction schemes shown below. Further, these materials can be isolated in enantiomerically pure form using standard methods including but not limited to: chiral HPLC, chiral synthesis, chemical or chromatographic separation of chiral derivatives of the 1,1'-dihydroxy-2,2'-binaphthalenes, e.g. via diastereomeric esters, urethanes, carbonates, and the like. The material 1,1'-dihydroxy-3,3'-diphenyl-2,2'-binaphthalene may be prepared and resolved via the brucine salt by one skilled in the art employing the oxidative coupling of 1-hydroxy-3-phenylnaphthalene as reported by W. D. Wulff, et. al., in *Organic Process Research Development* (2011), 15, 1089-1107. The materials (2R)-3,3'-diphenyl-[2,2'-binaphthalene]-1,1'-diol, (2S)-3,3'-diphenyl-[2,2'-binaphthalene]-1,1'-diol, (3R)-2,2'-diphenyl-[3,3'-biphenanthrene]-4,4'-diol, (3S)-2,2'-diphenyl-[3,3'-biphenanthrene]-4,4'-diol may be purchased from Sigma-Aldrich Chemical Company, St. Louis, Mo. The materials (2S)-8,8'-dimethyl-3,3'-diphenyl-[2,2'-binaphthalene]-1,1'-diol, (2R)-8,8'-dimethyl-3,3'-diphenyl-[2,2'-binaphthalene]-1,1'-diol, (2S)-3,3',8,8'-tetraphenyl-[2,2'-binaphthalene]-1,1'-diol, and (2R)-3,3',8,8'-tetraphenyl-[2,2'-binaphthalene]-1,1'-diol may be prepared by one skilled in the art by the procedures reported by W. D. Wulff, et. al., in *Journal of the American Chemical Society* (2009), 131(40), 14355-14364. The material 3,3'-diphenyl-[2,2'-bibenzo[b]naphtho[2,1-d]furan]-1,1'-diol may be prepared by the procedure of Arch Development Corp. WO2000056691 (2000). The material 8-methoxy-3-phenyl-1-naphthalenol may be prepared by the procedure of K. Suzuki, et. al., in *Angewandte Chemie International Edition* (2006), 45, 6294-6296. The material 3,4-diphenyl-1-naphthalenol may be prepared by the procedure of S. Ma, et. al., in *Chemistry-A European Journal* (2009), 15(42), 11083-11086. The materials 3-(4-chlorophenyl)-1-naphthalenol and 3-(3,4-dichlorophenyl)-1-naphthalenol may be prepared by the procedure of Sandoz-Wander Incorp. U.S. Pat. No. 3,761,526 (1973). The material 3,4-dimethyl-1-phenanthrenol may be prepared by the procedure of E. Marvell, et. al., in *Journal of Organic Chemistry* (1977), 42(23), 3783-3784. The materials 3,3'-dimethyl-[2,2'-binaphthalene]-1,1'-diol and 3,3'-didecyl-[2,2'-binaphthalene]-1,1'-diol may be prepared by the procedure of G. B. Schuster and R. Redic in *Journal of Photochemistry and Photobiology A: Chemistry* (2006), 179, 66-74. Chiral ketals of 1,1'-dihydroxy-2,2'-binaphthalenes may be prepared by analogy to the procedures for 1,1'-binaphthalenes described by G. B. Schuster and M. Zhang in *Journal of the American Chemical Society* (1994), 116, 4852-4857 and Merck Patent GMBH WO2002034739 (2002).

The esters of chiral 1,1'-dihydroxy-2,2'-binaphthalenes may be prepared by one skilled in the art, as for example shown in Scheme 1 below for Inv-2 by, or by analogy to, the reaction of carboxylic acid chlorides with chiral 1,1'-dihydroxy-2,2'-binaphthalenes, or by the reaction of carboxylic acids with chiral 1,1'-dihydroxy-2,2'-binaphthalenes in the presence of dicyclohexylcarbodiimide with a catalytic amount of dimethylaminopyridine. Other compounds of the invention can be prepared via modifications of these procedures or via implementation of reactions know to those skilled in the art.

Scheme 1.

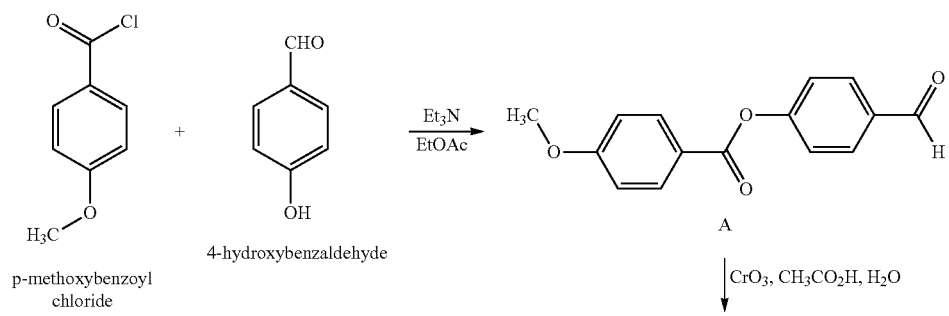

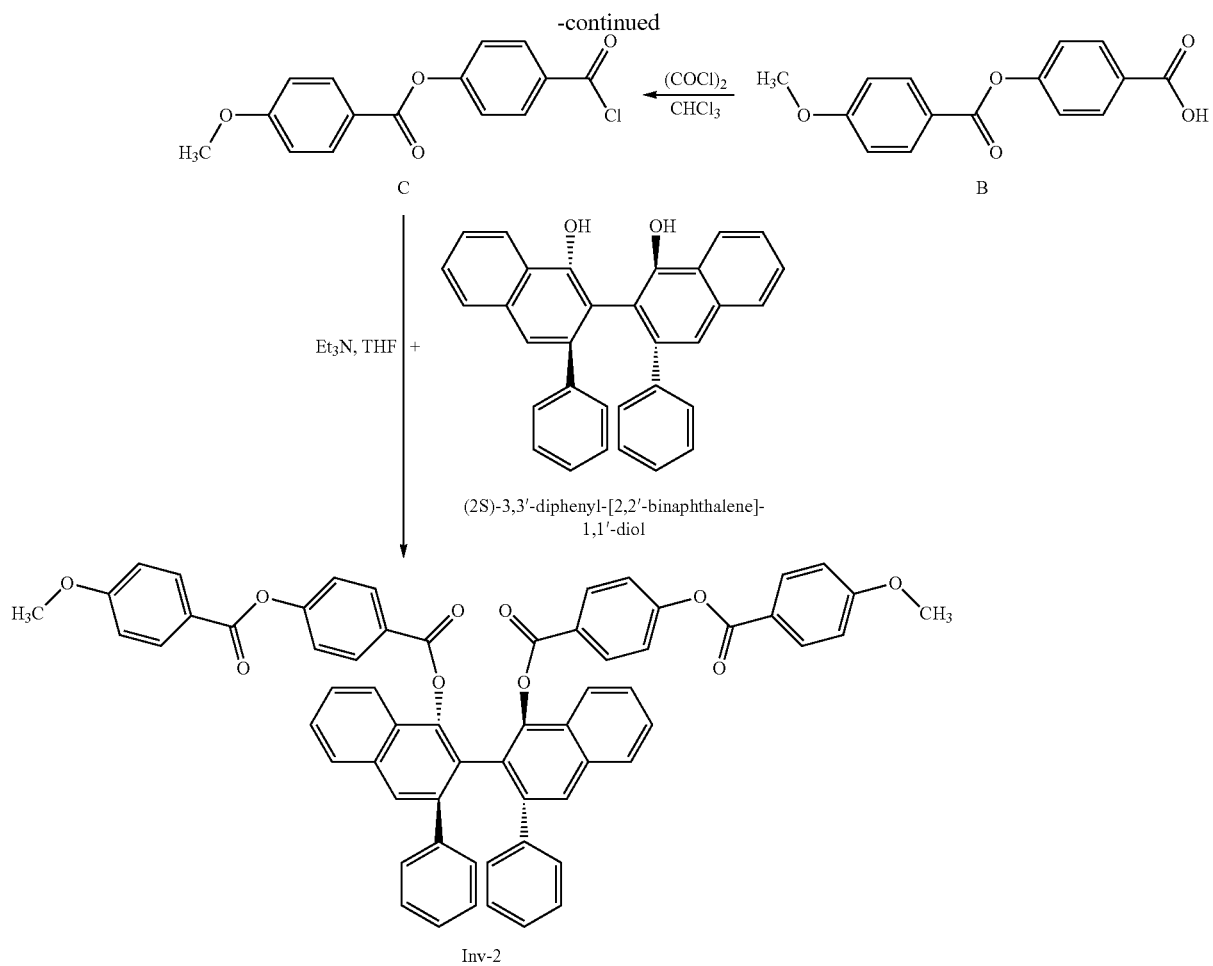

EXAMPLES

The following examples are presented to illustrate the practice of this invention, but are not meant to limit it in any way.

Preparation of Inv-1

(2S)-3,3'-Diphenyl-[2,2'-binaphthalene]-1,1'-[di(4-hexyloxybenzoate)], Inv-1

Into a 50 mL single neck round bottom flask was placed 0.44 gram (1.0 mmol) of (2S)-3,3'-diphenyl[2,2'-binaphthalene]-1,1'-diol (CAS 147702-14-5), 15 mL of ethyl acetate (CAS 141-78-6, Acros Organics) and a magnetic stirring bar. The mixture was stirred magnetically at room temperature for 5 minutes and 0.45 grams (4.5 mmol) of triethylamine (CAS 121-44-8, Acros Organics) was added all at once. The mixture was stirred at room temperature for 5 minutes and a solution of 4-(hexyloxy)benzoyl chloride (CAS 39649-71-3, Acros Organics) in 3 mL of ethyl acetate was added dropwise over a period of 1 minute. A white precipitate of triethylamine hydrochloride formed. The heterogeneous mixture was stirred at room temperature for one hour, then placed in a pre-heated oil bath at 60° C. and heated at 60° C. for 60 hours. After stirring for this time the light yellow colored product mixture was removed from the oil bath, cooled to room temperature and filtered using medium filter paper on a Buchner funnel to remove the precipitated triethylamine hydrochloride. The filtrate was chilled in ice water to precipitate additional triethylamine hydrochloride which was removed by filtration. The filtrate was concentrated to dryness in vacuo to afford a yellow oil of collected weight 1.12 grams. This material was chromatographed on a flash column of silica gel (Acros Organics silica gel 60A, 0.035-0.070 mm, column size 2 cm×40 cm) slurry packed in 5% ethyl acetate/95% hexane. The column was eluted under mild air pressure taking 50 mL fractions. The desired product eluted in fractions 7-10 using 5% ethyl acetate/95% hexane affording 0.70 grams of an amorphous white solid after solvent removal in vacuo. The product was crystallized by dissolving in 6 mL of dichloromethane which was added dropwise to 75 ml of boiling absolute ethanol (CAS 64-17-5, Acros Organics) with rapid magnetic stirring. By boiling the volume was reduced to 50 mL. The solution was allowed to stand at room temperature for one hour, then in ice/water for 30 minutes. The resulting white needle-like crystals were collected on medium filter paper, washed with 5 mL ethanol, then 5 mL hexane, then dried. The crystallization afforded 0.37 grams of white needle product, m.p.=190-192° C. This material was pure chromatographically. NMR (CDCl$_3$) 8.14 (pseudo d, 4H), 7.92 (broad s, 2H), 7.80 (pseudo d, 2H), 7.57 (pseudo s, 2H), 7.48 (pseudo d, 4H), 7.08 (pseudo t, 2H), 6.96 (pseudo t, 4H), 6.82 (m, 8H), 3.95 (t, 4H), 1.74 (m, 4H), 1.37-1.32 (m, 12H), 0.93 (t, 6H).

Preparation of Inv-2

4-(4'-Methoxybenzoyloxy)benzaldehyde, CAS 56800-26-1, Compound A Scheme 1

Into a 500 mL three neck round bottom flask was placed 12.2 grams (0.1 moles) of 4-hydroxybenzaldehyde (CAS 123-08-0, Sigma Aldrich Chemical Company), 12.15 grams of triethylamine (CAS 121-44-8, Acros Organics), and 200 mL of ethyl acetate (CAS 141-78-6, Acros Organics). The flask was fitted with a thermometer, 100 mL pressure equalized dropping funnel, condenser with nitrogen inlet and magnetic stirring bar. The mixture was stirred at room temperature, then a solution of 17.9 grams (0.105 moles) of p-methoxy benzoyl chloride (CAS 100-07-2, Sigma Aldrich Chemical Company) in 50 mL of ethyl acetate was added dropwise over a period of 20 minutes. The reaction developed a white precipitate and spontaneously heated to a temperature of 35° C. The heterogeneous reaction mixture was stirred at room temperature for one hour then placed in a pre-heated oil bath at 40° C. and heated with stirring for an additional two hours. After cooling to room temperature the product mixture was filtered through medium filter paper on a Buchner funnel to remove triethylamine hydrochloride. The filtrate was concentrated to dryness at 45° C. in vacuo to afford a collected weight of 26.55 grams of off-white solid. The product was crystallized from 100 mL of absolute ethanol (CAS 64-17-5, Acros Organics) by heating to boiling then allowing the solution to cool to room temperature over 90 minutes, then chilled in ice water for one hour. The product of collected weight 24.1 grams was chromatographically pure (TLC, 30% ethyl acetate/70% hexane, Rf=0.61), m.p.=87-88° C. (literature melting point=89° C., J. McIntyre, et. al., *Mol. Cryst. Liq. Crys.* (1982), 80, 105-118).

4-(4'-Methoxybenzoyloxy)benzoic acid, CAS 52899-69-1, Compound B Scheme 1

Into a 500 mL three neck round bottom flask equipped with condenser with drying tube, 125 mL pressure equalized dropping funnel, thermometer and magnetic stir bar was added 10.0 grams (0.04 moles) of 4-(4'-methoxybenzoyloxy)benzaldehyde (prepared as above) and 175 mL of 90% acetic acid. The mixture was stirred at room temperature for 30 minutes until homogeneous resulting in a clear colorless solution. To the stirred reaction mixture was added a solution of 12.0 grams (0.12 moles) of chromium trioxide in 120 mL of 60% acetic acid via a dropping funnel over a period of 30 minutes. A 5° C. exotherm was noted during addition and a precipitate formed. The reaction mixture was heated at 80° C. with stirring for 22 hours. The resulting deep green product mixture was allowed to cool to room temperature with stirring then poured into 400 mL distilled water with rapid stirring. The insoluble product was collected on medium filter paper by suction filtration and washed with 4×100 mL distilled water to afford a white crystalline product. The product was air dried to afford 9.2 grams of crude product. The product was crystallized by dissolving in 135 mL of glacial acetic acid at boiling, then allowed to stand at room temperature for 2 hours. The crystalline product was collected on medium filter paper by suction filtration, washed with 1×50 mL glacial acetic acid, 3×50 mL hexane, and air dried to afford 8.03 grams of white needles, m.p.=215-216° C.

NMR (DMSO) 13.1 (broad s, 1H), 8.1 (m, 4H), 7.4 (d, 2H), 7.1 (d, 2H), 3.9 (s, 3H).

4-[(4'-Methoxybenzoyl)oxy]benzoyl chloride, CAS 52899-54-4, Compound C of Scheme 1

Into a 100 mL three neck round bottom flask was placed a magnetic stir bar, 1.64 grams (6 mmol) of 4-(4'-methoxybenzoyloxy)benzoic acid (CAS 52899-69-1, as prepared above), and 25 mL chloroform (CAS 865-49-6, Sigma-Aldrich Chem. Co.). To the magnetically stirred slurry was added 4 drops of dimethylformamide (CAS 68-12-2, Alfa-Aesar Chemical Co.) and the reaction was placed under a nitrogen atmosphere then placed in an ice water bath and chilled to 5-10° C. To the stirred heterogeneous mixture was added 2.28 grams (18 mmol) of oxalyl chloride (CAS 79-37-8, Afla-Aesar Chem. Co.) dropwise from a capillary pipet over approximately 1 minute. The reaction was then removed from the ice bath and stirred at room temperature for 1 hour. The resulting heterogeneous mixture was placed in a pre-heated 40° C. oil bath and warmed with stirring at 40° C. for 30 minutes. The homogeneous product mixture was removed from the oil bath and concentrated to dryness in vacuo to afford an off-white solid. To the flask was added 25 mL chloroform and concentrated to dryness a second time to remove residual oxalyl chloride. The product mixture afforded an off-white solid. The collected weight was 2.0 grams which was used without further purification.

(2S)-3,3'-Diphenyl-[2,2'-binaphthalene]-1,1'-[di[4-(4'-methoxybenzoyl)oxy]benzoate], Inv-2

Into a 100 mL single neck round bottom flask was placed 0.44 gram (1.0 mmol) of (2S)-3,3'-diphenyl[2,2'-binaphthalene]-1,1'-diol (CAS 147702-14-5), and 10 mL of tetrahydrofuran (CAS 109-99-9, Acros Organics) and a magnetic stirring bar. The mixture was stirred at room temperature and 1.5 grams (15 mmol) of triethylamine (CAS 121-44-8, Acros Organics) was added all at once. The mixture was stirred at room temperature and a warmed solution of 4-[(4'-methoxybenzoy)oxy]benzoyl chloride (as prepared above) in 20 mL tetrahydrofuran was added over an approximately 2 minute period. A white precipitate of triethylamine hydrochloride formed immediately. The reaction was placed in a 60° C. pre-heated oil bath and heated at 60° C. for 48 hours. The product mixture was removed from the oil bath, cooled to room temperature and filtered through medium filter paper on a Buchner funnel to remove the insoluble triethylamine hydrochloride precipitate. The filtrate was concentrated to dryness in vacuo to afford 2.52 grams of crude product. This material was chromatographed on a flash column of silica gel (Acros Organics silica gel 60A, 0.035-0.070 mm, column size 4.5 cm×36 cm) slurry packed in 10% ethyl acetate/90% hexane. The column was eluted under mild air pressure taking 100 mL fractions and gradually increasing the percentage of ethyl acetate in the eluting solvent. The desired product eluted in fractions 5-20 using 30% ethyl acetate/70% hexane affording 1.12 grams of off-white powder after solvent removal in vacuo. The product was crystallized once from 250 ml absolute ethanol, then recrystallized by dissolving in 15 mL dichloromethane (CAS 75-09-2, Sigma Aldrich Chemical Company) which was slowly added to 300 mL absolute ethanol (CAS 64-17-5, Acros Organics) while heating on a hot plate. The volume was reduced to 175 mL then allowed to slowly cool with stirring. The product precipitated as a fine white powder and was collected with medium filter paper on a Buchner funnel, then dried under medium vacuum to afford 0.62 grams of white powder, m.p.=206-208° C. This material was pure chromatographically. NMR (CDCl$_3$) 8.25 (pseudo d, 4H), 8.15 (pseudo d, 4H), 7.91 (broad s, 2H), 7.84 (pseudo d, 2H), 7.63 (pseudo s, 2H), 7.50 (m, 4H), 7.23 (m, 4H), 7.13 (pseudo t, 2H), 7.01 (m, 8H), 6.89 (m, 4H), 3.90 (s, 6H).

Preparation of Inv-13

4-(Benzoyloxy)benzoic acid (CAS 28547-23-1) was prepared from benzoyl chloride (CAS 98-88-4, Sigma-Aldrich Chem. Co.) and 4-hydroxybenzoic acid (CAS 99-96-7, Sigma-Aldrich Chem. Co.) in aqueous sodium hydroxide using the procedure of C. Wu, et. al., *Journal of Applied Polymer Science*, (2004), 92, 2693-2697; m.p.=223-224° C.

4-(Benzoyloxy)benzoyl chloride, CAS 58860-84-7

Into a 100 mL three neck round bottom flask was placed a magnetic stir bar, 1.1 grams (4.5 mmol) of 4-(benzoyloxy) benzoic acid (CAS 28547-23-1, as prepared above), and 20 mL chloroform (CAS 865-49-6, Sigma-Aldrich Chem. Co.). To the magnetically stirred slurry was added 3 drops of dimethylformamide (CAS 68-12-2, Alfa-Aesar Chemical Co.) and the reaction was placed under a nitrogen atmosphere then placed in an ice water bath and chilled to 5-10° C. To the stirred heterogeneous mixture was added 1.53 grams (12 mmol) of oxalyl chloride (CAS 79-37-8, Afla-Aesar Chem. Co.) dropwise from a capillary pipet over approximately 1 minute. The reaction was then removed from the ice bath and stirred at room temperature for 1 hour. The resulting nearly homogeneous mixture was placed in a pre-heated 40° C. oil bath and warmed with stirring at 40° C. for one hour. The homogeneous product mixture was removed from the oil bath and concentrated to dryness in vacuo to afford an off-white solid. To the flask was added 25 mL chloroform and concentrated to dryness a second time to remove residual oxalyl chloride. The product mixture afforded an off-white solid. The collected weight was 1.2 grams which was used without further purification.

(2S)-3,3'-Diphenyl-[2,2'-binaphthalene]-1,1'-[di[4-(benzoyl)oxy]benzoate], Inv-13

Into a 100 mL single neck round bottom flask was placed 0.31 gram (0.7 mmol) of (2S)-3,3'-diphenyl[2,2'-binaphthalene]-1,1'-diol (CAS 147702-14-5), and 10 mL of tetrahydrofuran (CAS 109-99-9, Acros Organics) and a magnetic stirring bar. The mixture was stirred at room temperature and 1.12 grams (11.2 mmol) of triethylamine (CAS 121-44-8, Acros Organics) was added all at once. The mixture was stirred at room temperature and a warmed solution of 1.2 grams of 4-(benzoyloxy)benzoyl chloride (as prepared above) in 15 mL tetrahydrofuran was added over an approximately 2 minute period. A white precipitate of triethylamine hydrochloride formed immediately. The reaction was placed in a 60° C. pre-heated oil bath and heated at 60° C. for 48 hours. The product mixture was removed from the oil bath, cooled to room temperature, diluted with 50 mL of ethyl acetate, and filtered through medium filter paper on a Buchner funnel to remove the insoluble triethylamine hydrochloride precipitate. The filtrate was concentrated to dryness in vacuo to afford 1.52 grams of crude product. This material was chromatographed on a flash column of silica gel (Acros Organics silica gel 60A, 0.035-0.070 mm, column size 4.5 cm×36 cm) slurry packed in 10% ethyl acetate/90% hexane. The column was eluted under mild air pressure taking 100 mL fractions and gradually increasing the percentage of ethyl acetate in the eluting solvent. The desired product eluted in fractions 4-10 using 20% ethyl acetate/80% hexane affording 0.51 grams of white powder after solvent removal in vacuo. The product was crystallized by dissolving in 5 mL dichloromethane (CAS 75-09-2, Sigma Aldrich Chemical Company) which was slowly added to 50 mL absolute ethanol (CAS 64-17-5, Acros Organics) while heating on a hot plate. The volume was reduced to 40 mL then allowed to slowly cool with stirring, then chilled in ice/water for one hour. The crystalline product was collected with medium filter paper on a Buchner funnel, washed 1×5 mL ethanol, then 2×10 mL hexane, then dried under medium vacuum to afford 0.46 grams of white powder, m.p.=272-274° C. This material was pure chromatographically. NMR (CDCl$_3$) 8.27 (pseudo d, 4H), 8.21 (pseudo d, 4H), 7.91 (broad s, 2H), 7.85 (pseudo d, 2H), 7.64 (m, 4H), 7.51 (m, 8H), 7.27 (m, 4H), 7.13 (pseudo t, 2H), 7.01 (m, 4H), 6.89 (m, 4H).

Preparation of Inv-22

(2S)-3,3'-Diphenyl-[2,2'-binaphthalene]-1,1'-[di(1-naphthoate)], Inv-22

Into a 100 mL single neck round bottom flask was placed 0.31 gram (0.7 mmol) of (2S)-3,3'-diphenyl-[2,2'-binaphthalene]-1,1'-diol (CAS 147702-14-5), and 10 mL of tetrahydrofuran (CAS 109-99-9, Acros Organics) and a magnetic stirring bar. The mixture was stirred at room temperature and 1.12 grams (11.2 mmol) of triethylamine (CAS 121-44-8, Acros Organics) was added all at once. The mixture was stirred at room temperature and a solution of 0.86 grams (4.5 mmol) of 1-naphthoyl chloride (CAS 879-18-5, Sigma-Aldrich Chem. Co.) in 15 mL tetrahydrofuran was added over an approximately 2 minute period. A white precipitate of triethylamine hydrochloride formed immediately. The reaction was placed in a 60° C. pre-heated oil bath and heated at 60° C. for 60 hours. The product mixture was removed from the oil bath, cooled to room temperature, diluted with 50 mL of ethyl acetate, and filtered through medium filter paper on a Buchner funnel to remove the insoluble triethylamine hydrochloride precipitate. The filtrate was concentrated to dryness in vacuo to afford 1.23 grams of crude product. This material was chromatographed on a flash column of silica gel (Acros Organics silica gel 60A, 0.035-0.070 mm, column size 4.5 cm×36 cm) slurry packed in 10% ethyl acetate/90% hexane. The column was eluted under mild air pressure taking 100 mL fractions and gradually increasing the percentage of ethyl acetate in the eluting solvent. The desired product eluted in fractions 8-12 using 20% ethyl acetate/80% hexane affording 0.50 grams of white powder after solvent removal in vacuo. The product was crystallized by dissolving in 6 mL dichloromethane (CAS 75-09-2, Sigma Aldrich Chemical Company) which was slowly added to 40 mL absolute ethanol (CAS 64-17-5, Acros Organics) while heating on a hot plate. The volume was reduced to 30 mL then allowed to slowly cool with stirring, then chilled in ice/water for 30 minutes. The crystalline product was collected with medium filter paper on a Buchner funnel, washed 2×5 mL ethanol, then 1×10 mL hexane, then dried under medium vacuum to afford 0.26 grams of off-white powder, m.p.=141-143° C. This material was pure chromatographically. NMR (CDCl$_3$) 8.87 (pseudo d, 2H), 8.42 (broad s, 2H), 8.04 (broad s, 2H), 7.95 (pseudo d, 2H), 7.83 (m, 4H), 7.67 (pseudo s, 2H), 7.46 (m, 8H), 7.29 (pseudo t, 2H), 7.15 (pseudo t, 2H), 7.02 (m, 8H).

Preparation of Inv-23

6-(Benzyloxy)-2-naphthoic acid (CAS 114804-77-2) was prepared from 6-hydroxy-2-naphthoic acid (CAS 16712-64-

4, TCI America Chemical Company) according to the procedure of R. Dabrowski, et. al., *Ferroelectrics* (2006), 343, 11-18, m.p=252-254° C.

6-(Benzyloxy)-2-naphthalene carbonyl chloride, CAS 122179-30-0

Into a 100 mL three neck round bottom flask was placed a magnetic stir bar, 1.25 grams (4.5 mmol) of 6-(benzyloxy)-2-naphthoic acid (CAS 114804-77-2, as prepared above), and 20 mL chloroform (CAS 865-49-6, Sigma-Aldrich Chem. Co.). To the magnetically stirred slurry was added 3 drops of dimethylformamide (CAS 68-12-2, Alfa-Aesar Chemical Co.) and the reaction was placed under a nitrogen atmosphere then placed in an ice water bath and chilled to 5-10° C. To the stirred heterogeneous mixture was added 1.53 grams (12 mmol) of oxalyl chloride (CAS 79-37-8, Alfa-Aesar Chem. Co.) dropwise from a capillary pipet over approximately 1 minutes. The reaction was then removed from the ice bath and stirred at room temperature for 1 hour. The resulting nearly homogeneous light yellow mixture was placed in a pre-heated 40° C. oil bath and warmed with stirring at 40° C. for 1 hour. The product mixture was removed from the oil bath, filtered through fine filter paper to remove trace particulates, and then the filtrate was concentrated to dryness in vacuo to afford an off-white solid. To the flask was added 30 mL chloroform and concentrated to dryness a second time to remove residual oxalyl chloride. The product mixture afforded an off-white solid. The collected weight was 1.34 grams which was used without further purification.

(2S)-3,3'-Diphenyl-[2,2'-binaphthalene]-1,1'-[di[2-(6-benzyloxy)naphthoate]], Inv-23

Into a 100 mL single neck round bottom flask was placed 0.31 gram (0.7 mmol) of (2S)-3,3'-diphenyl[2,2'-binaphthalene]-1,1'-diol (CAS 147702-14-5), and 10 mL of tetrahydrofuran (CAS 109-99-9, Acros Organics) and a magnetic stirring bar. The mixture was stirred at room temperature and 1.12 grams (11.2 mmol) of triethylamine (CAS 121-44-8, Acros Organics) was added all at once. The mixture was stirred at room temperature and a solution of 1.34 grams (4.5 mmol) of 6-(benzyloxy)-2-naphthalene carbonyl chloride, CAS 122179-30-0, in 15 mL tetrahydrofuran was added over an approximately 1 minute period. A white precipitate of triethylamine hydrochloride formed immediately. The reaction was placed in a 60° C. pre-heated oil bath and heated at 60° C. for 60 hours. The product mixture was removed from the oil bath, cooled to room temperature, diluted with 50 mL of ethyl acetate, and filtered through medium filter paper on a Buchner funnel to remove the insoluble triethylamine hydrochloride precipitate. The filtrate was concentrated to dryness in vacuo to afford 1.55 grams of crude product. This material was chromatographed on a flash column of silica gel (Acros Organics silica gel 60A, 0.035-0.070 mm, column size 4.5 cm×40 cm) slurry packed in 10% ethyl acetate/90% hexane. The column was eluted under mild air pressure taking 100 mL fractions and gradually increasing the percentage of ethyl acetate in the eluting solvent. The desired product eluted in fractions 28-33 using 20% ethyl acetate/80% hexane affording 0.51 grams of white amorphous solid after solvent removal in vacuo. The product was crystallized by dissolving in 10 mL dichloromethane (CAS 75-09-2, Sigma Aldrich Chemical Company) which was slowly added to 100 mL absolute ethanol (CAS 64-17-5, Acros Organics) while heating on a hot plate. The volume was reduced to 75 mL then allowed to slowly cool for 12 hours. The crystalline product was collected with medium filter paper on a Buchner funnel, washed 2×5 mL ethanol, then 1×10 mL hexane, then dried under medium vacuum. The recrystallization procedure was repeated once more to afford 0.45 grams of white fine crystals, m.p.=237-238° C. This material was pure chromatographically. NMR (CDCl$_3$) 8.73 (broad s, 2H), 8.19 (pseudo d, 2H), 8.01 (broad s, 2H), 7.78 (pseudo d, 2H), 7.69 (m, 4H), 7.61 (pseudo s, 2H), 7.53-7.35 (m, 14H), 7.24 (pseudo d of d, 2H), 7.19 (m, 2H), 7.13 (pseudo t, 2H), 7.02 (pseudo t, 4H), 6.92 (pseudo d, 4H), 5.19 (s, 4H).

Preparation of Inv-43

4'-Methoxy[1,1'-biphenyl]-4-carboxylic acid chloride, CAS 67132-14-3

Into a 100 mL three neck round bottom flask was placed a magnetic stir bar, 1.03 grams (4.5 mmol) of 4'-methoxybiphenyl-4-carboxylic acid (CAS 725-14-4, Alfa-Aesar Chemical Co.), and 20 mL chloroform (CAS 865-49-6, Sigma-Aldrich Chem. Co.). To the magnetically stirred slurry was added 3 drops of dimethylformamide (CAS 68-12-2, Alfa-Aesar Chemical Co.) and the reaction was placed under a nitrogen atmosphere then placed in an ice water bath and chilled to 5-10° C. To the stirred heterogeneous mixture under nitrogen was added 1.53 grams (12 mmol) of oxalyl chloride (CAS 79-37-8, Alfa-Aesar Chem. Co.) dropwise from a capillary pipet over approximately 1 minutes. The reaction was then removed from the ice bath and stirred at room temperature for 1 hour. The resulting nearly homogeneous light yellow mixture was placed in a pre-heated 40° C. oil bath and warmed with stirring at 40° C. for 1 hour. The product mixture was removed from the oil bath, filtered through fine filter paper to remove trace particulates, and then the filtrate was concentrated to dryness in vacuo. To the flask was added 50 mL chloroform and concentrated to dryness a second time to remove residual oxalyl chloride. The product mixture afforded a cream-white solid. The collected weight was 1.14 grams which was used without further purification.

(2S)-3,3'-Diphenyl-[2,2'-binaphthalene]-1,1'-[di[4-(4'-methoxyphenyl)benzoate]], Inv-43

Into a 100 mL single neck round bottom flask was placed 0.31 gram (0.7 mmol) of (2S)-3,3'-diphenyl[2,2'-binaphthalene]-1,1'-diol (CAS 147702-14-5), and 10 mL of tetrahydrofuran (CAS 109-99-9, Acros Organics) and a magnetic stirring bar. The mixture was stirred at room temperature and 1.12 grams (11.2 mmol) of triethylamine (CAS 121-44-8, Acros Organics) was added all at once. The mixture was stirred at room temperature and a solution of 1.14 grams (4.5 mmol) of 4'-methoxy[1,1'-biphenyl]-4-carboxylic acid chloride, CAS 67132-14-3, in 15 mL tetrahydrofuran was added over an approximately 1 minute period. A white precipitate of triethylamine hydrochloride formed immediately. The reaction was placed in a 60° C. pre-heated oil bath and heated at 60° C. for 60 hours. The product mixture was removed from the oil bath, cooled to room temperature, diluted with 50 mL of ethyl acetate, and filtered through medium filter paper on a Buchner funnel to remove the insoluble triethylamine hydrochloride precipitate. The filtrate was concentrated to dryness in vacuo to afford 1.03 grams of crude product. This material was chromatographed on a flash column of silica gel (Acros Organics silica gel 60A, 0.035-0.070 mm, column size 4.5 cm×40 cm) slurry packed in 10% ethyl acetate/90% hexane. The column was eluted under mild air pressure taking 100 mL fractions and gradually increasing the percentage of ethyl acetate in the eluting solvent. The desired product eluted in fractions 28-40 using 30% ethyl acetate/70% hexane affording 0.39 grams of off-white crystals after solvent removal in vacuo. The product was re-chromatographed on a flash column of silica gel (Acros Organics silica gel 60A, 0.035-0.070 mm, column size 2 cm×40 cm) slurry packed in 75% dichloromethane/25% hexane. The column was eluted under mild air pressure taking 50 mL fractions. The desired product eluted in fractions 7-11 using 75% dichloromethane/25% hexane affording 0.23 grams of white powder after solvent removal in vacuo. The product was crystallized by dissolving in 10 mL dichloromethane (CAS 75-09-2, Sigma Aldrich Chemical Company) which was slowly added to 75 mL absolute ethanol (CAS 64-17-5, Acros Organics) while heating on a hot plate. The volume was reduced to 50 mL then allowed to slowly cool for 2 hours. The crystalline product was collected with medium filter paper on a Buchner funnel, washed 2×5 mL ethanol, then 2×5 mL hexane, then dried in a drying vacuum oven for 4 hours (95° C., medium vacuum) to afford 0.20 grams of white fine needles, m.p.=277-278° C. This material was pure chromatographically. NMR (CDCl$_3$) 8.25 (pseudo d, 4H), 7.95 (pseudo s, 2H), 7.82 (pseudo d, 2H), 7.62-7.46 (m, 14H), 7.12 (pseudo t, 2H), 7.03-6.96 (m, 8H), 6.89 (pseudo d, 4H), 3.86 (s, 6H).

Fabrication of Test Cell

The display cell is fabricated from two 0.7 mm thick glass substrates (2 in×2 in) each coated with indium tin oxide (ITO), hard coat, and polyimide. The two glass pieces are held together with a gasket material and spacers to maintain a cell thickness of 5 microns. A small gap is left in the gasket material to fill the cell with the cholesteric liquid crystal mixture. The cholesteric liquid crystal mixture consists of a small percentage of the invented chiral material and a large percentage of a nematic liquid crystal (LC1) with high birefringence and high dielectric anisotropy. Prior to filling, the mixture is heated to isotropic to ensure that all components are mixed and the mixture is a homogeneous solution. Then, the mixture is vacuum filled into the cell. Once the cell is made, the cell is placed in an oven set to 100° C. to clear the liquid crystal to the isotropic. After 10 minutes, the cell is removed from the oven and the cell is allotted 30 minutes to cool to the focal conic texture. Once cooled, the cell is electrically switched to the planar texture with a voltage of 45 volts at a pulsewidth of 100 ms at a frequency of 250 Hz.

Evaluation of Chiral Material

To determine the helical twisting power of the invented chiral, the peak wavelength of the planar texture is measured using a Minolta spectrophotometer, which is comprised of an integrating sphere and a strobing white light source. Using the following equation, an approximate value for the HTP is calculated:

$$\beta = \frac{\bar{n}}{c}\left(\frac{1}{\lambda}\right),$$

where β is the helical twisting power, $\bar{n}$ is the refractive index of the nematic host, λ is the peak reflection wavelength of the current sample and c is the weight percent concentration of the chiral dopant. A chiral dopant with an HTP greater than 40 μm$^{-1}$ is interesting for further investigation. The measured peak wavelengths and HTPs of several examples are shown in Table 1.

TABLE 1

Amount of chiral material in cholesteric mixture and measured HTP for each invented material.

| Chiral | % of Chiral in Mixture | % of LC1 in Mixture | Measured Peak λ | Measured HTP |
|---|---|---|---|---|
| Inv-1 | %2.44 | %97.56 | nm 572 | 118 μm$^{-1}$ |
| Inv-2 | %2.22 | %97.78 | nm 565 | 131 μm$^{-1}$ |
| Inv-13 | %3.92 | %96.08 | nm 410 | 102 μm$^{-1}$ |
| Inv-17 | %3.06 | %96.94 | nm 490 | 111$^{-1}$ |
| Inv-23 | %3.02 | %96.98 | nm 498 | 117$^{-1}$ |
| Inv-44 | %3.38 | %96.62 | nm 540 | 90 μm$^{-1}$ |

The electro-optical properties are measured. For this measurement, a 300 W Xenon Arc Lamp is used. The light source emits light into a monochromator that separates the emitted light into a single wavelength of light. The cell is positioned normal to the light beam. The photodetector is already positioned so that if the sample is placed perpendicular to the light beam, the photodetector captures the reflection of the sample at an angle of 45°. Once the cell is aligned, using a LabVIEW program to control the equipment remotely, the spectrum is measured to determine maximum reflection of the cell at 45°. The setup is then set at the peak wavelength for the remaining measurements. Next, the response time for the cell to relax from the homeotropic state to the planar texture is measured. Then, the electro-optical response curve is measured, where the program sweeps through range of voltages measuring the reflectance at each voltage. For these measurements, a pulsewidth of 100 ms at a frequency of 250 Hz is used.

Many modifications and variations of the invention will be apparent to those of ordinary skill in the art in light of the foregoing disclosure. Therefore, it is to be understood that, within the scope of the appended claims, the invention can be practiced otherwise than has been specifically shown and described.

What is claimed is:

1. A liquid crystal composition comprising a chiral dopant compound represented by the following structure:

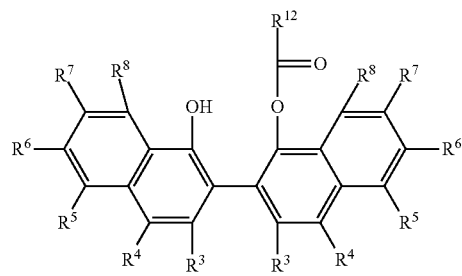

wherein:
R$^3$ is hydrogen, halogen, cyano, alkoxy, NHCOR$^9$, NHSO$_2$R$^9$, COOR$^9$, OCOR$^9$, aryl, alkyl, alkenyl, cycloalkyl, or heterocyclic all either substituted or unsubstituted;
R$^4$ is hydrogen, alkyl, aryl, alkenyl, cycloalkyl, or heterocyclic all either substituted or unsubstituted;
R$^5$, R$^6$, R$^7$, and R$^8$ are independently hydrogen, halogen, cyano, alkoxy, NHCOR$^9$, NHSO$_2$R$^9$, COOR$^9$, OCOR$^9$, aryl, alkyl, alkenyl, cycloalkyl, alkoxyaryl or heterocyclic all either substituted or unsubstituted, or combine with each other, or $R^5$ can combine with $R^4$, to form a carbocyclic or heterocyclic ring;

$R^9$ is alkyl, aryl, alkenyl, cycloalkyl, alkoxyaryl or heterocyclic all either substituted or unsubstituted;

$R^{12}$ is alkyl, alkoxy, aryl, naphthyl, styryl, alkenyl, cycloalkyl, cycloalkyloxy, alkoxyaryl or heterocyclic all either substituted or unsubstituted.

2. A liquid crystal composition of claim 1 comprising an enantiomerically excess of one enantiomer of said chiral dopant compound.

3. A liquid crystal composition of claim 1 wherein $R^{12}$ is aryl either substituted or unsubstituted as defined by: —$R^{12}$=—$(Y-K)_p$—Z: wherein K is a single bond or double bond or bivalent linking selected from the group consisting of: —C(=O)O—; —O(C=O)—; —CH$_2$CH$_2$—; —CH=CH—; —C≡C—; —OCH$_2$—; —CH$_2$O—; N=CH—; —CH=N—; —O(C=O)O—; —C≡C—C≡C—; —COCH=CH—; —CH=CHCO—; —O—; —S—; and SO$_2$; as long as oxygen atoms are not linked directly to one another; wherein Y and Z independently are optionally selected from the group consisting of: 1,4-phenylene in which, in addition, one or more methylene may be replaced by —N=; 1,4-cyclohexyl in which, in addition, one or more non-adjacent methylene units may be replaced by O or S; 1,4-cyclohexylene; 1,4-bicyclo[2.2.2]octylene; piperidine-1,4-diyl; decahydronaphthalene-1,6-diyl; and 1,2,3,4-tetrahydronaphthalene-1,6-diyl; wherein each of the Y or Z groups may be unsubstituted or mono-substituted or polysubstituted with halogen, cyano, isocyanato, or nitro groups, or alkyl, alkoxyl, or alkanoyl groups bearing 1-12 carbons where one or more hydrogens may be replaced with chlorine or fluorine; and wherein p=0, 1,2,3,4.

4. A liquid crystal composition of claim 1 wherein $R^3$ is an aryl group either substituted or unsubstituted.

5. A liquid crystal composition of claim 1 comprising said chiral dopant admixed with a liquid crystal material, wherein said chiral dopant compound is optionally in a polymerized form.

6. A liquid crystal composition of claim 5 further comprising a polymer binder in which domains of the liquid crystal material are dispersed.

7. A liquid crystal composition of claim 5 further comprising at least one of a catalyst, a sensitizer, a stabilizer, a co-reacting monomer, or a surface-active compound.

8. A liquid crystalline composition of claim 5 wherein the liquid crystalline composition is STN, TN, chiral nematic, or ferroelectric.

9. A liquid crystalline composition of claim 5 which is chiral nematic.

10. A liquid crystal display, electronic writer/tablet, electronic skin, optical element, or color filter comprising the liquid crystal composition of claim 5.

11. The display of claim 10 wherein the display is selected from the group consisting of a STN, TN, TFT-TN, guest-host, phase change, polymer free cholesteric texture, polymer stabilized cholesteric texture and ferroelectric display.

12. A liquid crystal composition comprising a chiral dopant compound represented by the following structure:

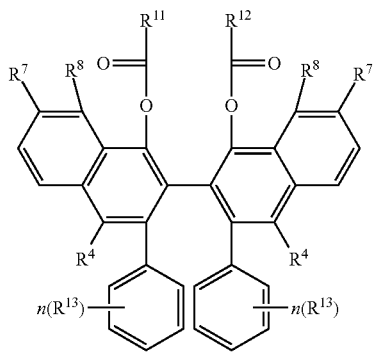

wherein:

$R^4$ is hydrogen, alkyl, aryl, alkenyl, cycloalkyl, or heterocyclic all either substituted or unsubstituted;

$R^7$, and $R^8$ are independently hydrogen, halogen, cyano, alkoxy, NHCOR$^9$, NHSO$_2$R$^9$, COOR$^9$, OCOR$^9$, aryl, alkyl, alkenyl, cycloalkyl, alkoxyaryl or heterocyclic all either substituted or unsubstituted, or combine to form a carbocyclic or heterocyclic ring;

$R^9$ is alkyl, aryl, alkenyl, cycloalkyl, alkoxyaryl or heterocyclic all either substituted or unsubstituted;

$R^{11}$ and $R^{12}$ are independently alkyl, alkoxy, aryl, naphthyl, styryl, alkenyl, cycloalkyl, cycloalkyloxy, alkoxyaryl or heterocyclic all either substituted or unsubstituted, or combine to form a carbocyclic or heterocyclic ring;

$R^{13}$ is hydrogen, halogen, cyano, alkoxy, NHCOR$^9$, NHSO$_2$R$^9$, COOR$^9$, OCOR$^9$, aryl, alkyl, alkenyl, cycloalkyl, or heterocyclic all either substituted or unsubstituted;

n is 1-5.

13. A liquid crystal composition of claim 12 comprising an enantiomerically excess of one enantiomer of said chiral dopant compound.

14. A liquid crystal composition of claim 12 wherein $R^{11}$ and $R^{12}$ are aryl either substituted or unsubstituted as defined by: —$R^{11}$ or —$R^{12}$=—$(Y-K)_p$—Z: wherein K is a single bond or double bond or bivalent linking selected from the group consisting of: —C(=O)O—; —O(C=O)—; —CH$_2$CH$_2$—; —CH=CH—; —C≡C—; —OCH$_2$—; —CH$_2$O—; —N=CH—; —CH=N—; —O(C=O)O—; —C≡C—C≡C—; —COCH=CH—; —CH=CHCO—; —O—; —S—; and SO$_2$; as long as oxygen atoms are not linked directly to one another; wherein Y and Z independently are optionally selected from the group consisting of: 1,4-phenylene in which, in addition, one or more methylene may be replaced by —N=; 1,4-cyclohexyl in which, in addition, one or more non-adjacent methylene units may be replaced by O or S; 1,4-cyclohexylene; 1,4-bicyclo[2.2.2]octylene; piperidine-1,4-diyl; decahydronaphthalene-1,6-diyl; and 1,2,3,4-tetrahydronaphthalene-1,6-diyl; wherein each of the Y or Z groups may be unsubstituted or mono-substituted or polysubstituted with halogen, cyano, isocyanato, or nitro groups, or alkyl, alkoxyl, or alkanoyl groups bearing 1-12 carbons where one or more hydrogens may be replaced with chlorine or fluorine; and wherein p=0, 1,2,3,4.

15. A liquid crystal composition of claim 12 comprising said chiral dopant admixed with a liquid crystal material, wherein said chiral dopant compound is optionally in a polymerized form.

16. A liquid crystal composition of claim 15 further comprising a polymer binder in which domains of the liquid crystal material are dispersed.

17. A liquid crystal composition of claim 15 further comprising at least one of a catalyst, a sensitizer, a stabilizer, a co-reacting monomer, or a surface-active compound.

18. A liquid crystalline composition of claim 15 wherein the liquid crystalline composition is STN, TN, chiral nematic, or ferroelectric.

19. A liquid crystalline composition of claim 15 which is chiral nematic.

20. A liquid crystal display, electronic writer/tablet, electronic skin, optical element, or color filter comprising the liquid crystal composition of claim 15.

21. The display of claim 20 wherein the display is selected from the group consisting of a STN, TN, TFT-TN, guest-host, phase change, polymer free cholesteric texture, polymer stabilized cholesteric texture and ferroelectric display.

* * * * *

UNITED STATES PATENT AND TRADEMARK OFFICE
CERTIFICATE OF CORRECTION

| | | |
|---|---|---|
| PATENT NO. | : 9,005,478 B2 | Page 1 of 1 |
| APPLICATION NO. | : 14/147730 | |
| DATED | : April 14, 2015 | |
| INVENTOR(S) | : Diehl et al. | |

It is certified that error appears in the above-identified patent and that said Letters Patent is hereby corrected as shown below:

In the specification:

Column 2, Line 56, please delete "Dec. 22, 2014" and replace it with -- Dec. 22, 2011 --

In the claims:

Column 45, Line 19, please delete "N=CH-" and replace it with -- -N=CH- --

Column 46, Line 46, please delete "-C=C" and replace it with -- -C=C- --

Signed and Sealed this
Sixth Day of October, 2015

Michelle K. Lee
*Director of the United States Patent and Trademark Office*